(12) United States Patent
Barnhizer et al.

(10) Patent No.: US 9,034,583 B2
(45) Date of Patent: May 19, 2015

(54) RAPID ENZYME-LINKED IMMUNOSORBENT ASSAY FOR DETECTION AND IDENTIFICATION OF PATHOGENS AND DETERMINATION OF ANTIMICROBIAL SUSCEPTIBILITY

(71) Applicants: Bret T. Barnhizer, Poland, OH (US); Jonathan P Faro, Houston, TX (US)

(72) Inventors: Bret T. Barnhizer, Poland, OH (US); Jonathan P Faro, Houston, TX (US)

(\*) Notice: Subject to any disclaimer, the term of this patent is extended or adjusted under 35 U.S.C. 154(b) by 0 days.

(21) Appl. No.: 14/256,694

(22) Filed: Apr. 18, 2014

(65) Prior Publication Data

US 2014/0315219 A1    Oct. 23, 2014

Related U.S. Application Data

(60) Provisional application No. 61/814,096, filed on Apr. 19, 2013.

(51) Int. Cl.
*G01N 33/53* (2006.01)
*G01N 33/571* (2006.01)
*G01N 33/569* (2006.01)
*C12Q 1/18* (2006.01)

(52) U.S. Cl.
CPC ........ *G01N 33/571* (2013.01); *G01N 33/56916* (2013.01); *C12Q 1/18* (2013.01)

(58) Field of Classification Search
None
See application file for complete search history.

(56) References Cited

U.S. PATENT DOCUMENTS 6,498,016 B1 \* 12/2002 Nahar et al. ................ 435/7.92
7,824,867 B2 \* 11/2010 Wang et al. .................. 435/7.1

\* cited by examiner

*Primary Examiner* — Brian J Gangle
(74) *Attorney, Agent, or Firm* — Acker Wood IP Law, LLC; Gwen R. Acker Wood

(57) ABSTRACT

The present invention provides a rapid, highly sensitive and specific enzyme-linked immunosorbent assay (ELISA), referred to as N-Assay, a device, and a kit, for detection and identification of microorganisms in a sample, in thirty minutes or less, with little or no interference from non-target microorganisms. The present invention also provides for simultaneous determination of antimicrobial susceptibility of microorganism in the N-Assay.

11 Claims, 19 Drawing Sheets

RAPID ENZYME-LINKED IMMUNOSORBENT ASSAY FOR DETECTION AND IDENTIFICATION OF PATHOGENS AND DETERMINATION OF ANTIMICROBIAL SUSCEPTIBILITY

CROSS REFERENCE TO RELATED APPLICATIONS

This application claims priority to U.S. Provisional Patent Application No. 61/814,096, filed Apr. 19, 2013, which is incorporated herein by reference in its entirety.

FIELD OF THE INVENTION

The invention relates to microbiological detection and identification assays and, more particularly, to a rapid, enzyme-linked immunosorbent assay for detection, identification and determination of antimicrobial susceptibility of microorganisms.

BACKGROUND OF THE INVENTION

Identification of a clinically relevant pathogen requires great time, expense and expertise. Once clinical suspicion is raised that an infection is present, cultures are typically obtained from relevant sites from the patient and the patient is started on empiric antibiotic treatment. Isolation of the offending microorganism currently is a long and arduous process that involves painstaking attention to detail, and begins with culture on select agar for 24 to 48 hours. For some pathogens, an enrichment step is used prior to culture in order to increase the sensitivity of the culture. Once a pathogen is identified, to determine the susceptibility of the pathogen to antimicrobial agents, the isolate needs to be sub-cultured for an additional 24 to 48 hours in the presence of select antibiotics in order to further guide treatment. The entire process of identification of a clinically relevant pathogen and determination of its antibiotic susceptibility may take at least 3 to 5 days.

In order to reduce the amount of time required to identify a pathogen and determine its susceptibility to an antibiotic, additional techniques may be employed. These include the use of chromogenic broth/agar to reduce the time spent during the initial culture step, or the use of nucleic acid amplification technology (NAAT) to identify a specific pathogen after an enrichment step. If resistance determinants commonly found in a specific pathogen are known, these may be used to identify resistant pathogens by NAAT, further decreasing the time required to identify a specific microorganism. For example, in the determination of antenatal maternal colonization by group B *streptococcus* (GBS), both chromogenic agar/broth and nucleic acid amplification detection strategies have been employed. However, in situations in which a negative result is obtained by NAAT, the CDC recommends that culture still be performed. Furthermore, culture is required if antibiotic susceptibility is desired. All of these techniques involve additional resources and training, and are not always readily available.

In a recent policy paper released by the Infectious Diseases Society of America (IDSA), a call was made for the development of more rapid tests for the identification of clinically relevant pathogens, with the goal of providing better direction to the clinician in providing targeted treatment. This public policy statement cites a known deficiency in the common practice of empirically treating infections, with the concern that this practice allows for resistance against antibiotics to develop, ultimately rendering our tools useless in treating these infections. While penicillin-resistant GBS has not yet been associated with clinical disease, resistance against clindamycin is prevalent. Furthermore, resistance of *Enterococcus* against vancomycin has increased, and very recently, a strain of *Neisseria gonorrhea* was found to be resistant to cephalosporins. These three disparate organisms illustrate a range in the response to our directed approach in both prophylaxis and treatment. Indeed, they illustrate an evolution in microbial defensive mechanisms against our available antibiotics. Resistance of *Enterococcus* to vancomycin is well established, and continues to be a pressing concern. Many have warned of the impending development of cephalosporin resistance with *gonorrhea*, and this has been recently documented. Finally, the routine practice of intrapartum prophylaxis against GBS has raised concern not only that GBS will develop resistance, but other organisms will eventually be selected for, and many fear that this is already occurring with the increased incidence of neonatal sepsis due to *E. coli*.

Early-onset neonatal sepsis has been shown to cause significant morbidity and mortality. Since the introduction of the CDC's guidelines for intrapartum chemoprophylaxis, the incidence of early-onset sepsis due specifically to GBS has decreased significantly. These guidelines recommend the antepartum screening of all pregnant patients between 35-37 weeks via a vaginal-rectal swab. For patients who are not able to be screened (preterm labor), the CDC recommends prophylaxis based on risk factors, including prematurity, history of an infant with GBS-sepsis, or prolonged rupture of membranes. While this approach has been widely accepted in the United States, there is concern that many patients are being exposed to antibiotics unnecessarily, and in doing so, antimicrobial resistance may develop.

Currently, isolation of GBS from a patient's vaginal-rectal specimen may occur one of two ways: culture, or by NAAT. Both methods have inherent strengths and weaknesses. Culture requires up to 48 hours, and samples may be overgrown by competing organisms. In addition, classic beta-hemolysis may be difficult to see in some clinical isolates, or completely absent. Moreover, when GBS is detected, additional steps are often required to ensure that false positives are ruled out. Recently, several products have become available which aid in the detection of GBS, with chromogenic broth/agar being the most notable.

NAAT offers great promise with the potential to streamline the process of pathogen detection. With this technique, a primer is generated which is targeted against DNA specific for GBS, and if GBS is present, even in very small amounts, it may be detected through amplification of the genetic material. Several commercial tests are available for detection of GBS, and one of these has been shown to allow for detection in less than 45 minutes. NAAT has deficiencies, however: the use of specialized equipment requires repeated measures for quality control and to prevent contamination; many laboratories will batch samples and run them at once, reducing the rapidity of the test; and NAAT does not allow for the detection of microbial strains which have developed de novo resistance. This is a significant shortcoming, since determination of de novo resistance of GBS against a specific antibiotic requires an additional culture period.

There exists an urgent need, therefore, for the development of a rapid assay with high specificity and sensitivity, which allows for simultaneous identification of a pathogen and for determination of the pathogen's antimicrobial susceptibility.

SUMMARY OF THE INVENTION

The present invention fulfills this need by providing a rapid enzyme-linked immunosorbent assay, referred to herein as "N-Assay," which overcomes the above-described shortcomings of current assays by providing a rapid assay, with high sensitivity and specificity, for detection and identification of a microorganism in a sample in as little as 30 minutes or less, as well as for determination of antimicrobial susceptibility of the microorganism.

In an aspect of the invention, there invention provides a method for rapid detection and identification of a microorganism in a sample. The method comprises preparing one or more serial dilutions of a microorganism; depositing the one or more serial dilutions into a separate well of a plurality of wells in a plate, said plurality of wells previously coated with an antibody specific for the microorganism, incubated overnight at 4° C.; washed, adding a blocking agent, and washed a second time; gently shaking the plurality of wells for about 15 minutes of time at room temperature; washing the plurality of wells; adding an enzyme-conjugated antibody specific for the microorganism to the plurality of wells and incubating the plurality of wells for about 7 minutes; washing the plurality of wells; adding a substrate specific to the enzyme conjugated to the antibody to the plurality of wells and incubating the plurality of wells for about 3 minutes; detecting and identifying the microorganism in wells showing a yellow color, or by reading at $OD_{450}$, wherein the method for detection and identification of the microorganism takes about 30 minutes or less.

In another aspect of the invention, the invention provides a method for rapid detection and identification of a microorganism in a sample and determination of susceptibility of the microorganism to an antibiotic in a sample, comprising preparing one or more serial dilutions of a microorganism in the presence or absence of an antibiotic; incubating the one or more serial dilutions of the microorganism in the presence or absence of the antibiotic for about 18 to 24 hours at 37° C.; depositing the one or more serial dilutions of the microorganism into a separate well of a plurality of wells in a plate, said plurality of wells previously coated with an antibody specific for the microorganism, incubated overnight at 4° C.; washed, adding a blocking agent, and washed a second time; gently shaking the plurality of wells for about 15 minutes of time at room temperature; washing the plurality of wells; adding an enzyme-conjugated antibody specific for the microorganism to the plurality of wells and incubating the plurality of wells for about 7 minutes; washing the plurality of wells; adding a substrate specific to the enzyme conjugated to the antibody to the plurality of wells and incubating the plurality of wells for about 3 minutes; detecting and identifying in about 30 minutes or less the microorganism in wells showing a yellow color, or by reading at $OD_{450}$, and when an identification has been made, determining the susceptibility of the identified microorganism to the antibiotic by seeing whether those wells containing the identified microorganism and the antibiotic show a yellow color or are read at $OD_{450}$, wherein no color or a reading at $OD_{450}$ indicates that the identified microorganism is susceptible to the antibiotic, and wherein yellow color or a reading at $OD_{450}$ indicates that the identified microorganism is not susceptible to the antibiotic.

Determination of the susceptibility of the microorganism to one or more antibiotics takes only an additional 24 hours, compared to current state of the art assays for determining microbial susceptibility to antimicrobials, such as antibiotics, which require between at least 3 to 5 days.

In another aspect of the invention, the invention provides a device for rapidly detecting and identifying a microorganism in a sample. The device comprises a plurality of wells in plate; a coating of an antibody specific for a microorganism deposited on surfaces of the plurality of wells; a wash liquid for preparing one or more serial dilutions of the microorganism, and for washing the plurality of wells, said serial dilutions of the microorganism deposited atop the coating in the plurality of wells; an enzyme-conjugated antibody specific for the microorganism which is deposited atop the serial dilutions of the microorganism; a substrate specific to the enzyme conjugated antibody which is deposited atop the enzyme-conjugated antibody which detects bound enzyme-conjugated antibody; and a stop solution which is deposited atop the substrate which stops reaction of the substrate with the enzyme-conjugated antibody, wherein the detection and the identification of the microorganism in the sample is accomplished in about 30 minutes or less.

In another aspect of the invention, the invention provides kits comprised of the above-described device so that the rapid N-Assay can be used as a point of care (POC) assay for microbial organisms in the field by users having limited training of microbiological testing and not requiring sophisticated laboratory equipment.

BRIEF DESCRIPTION OF THE DRAWINGS

A fuller understanding of the invention can be gained from the following description when read in conjunction with the accompanying drawings in which.

DETAILED DESCRIPTION OF THE INVENTION

Figure 1:
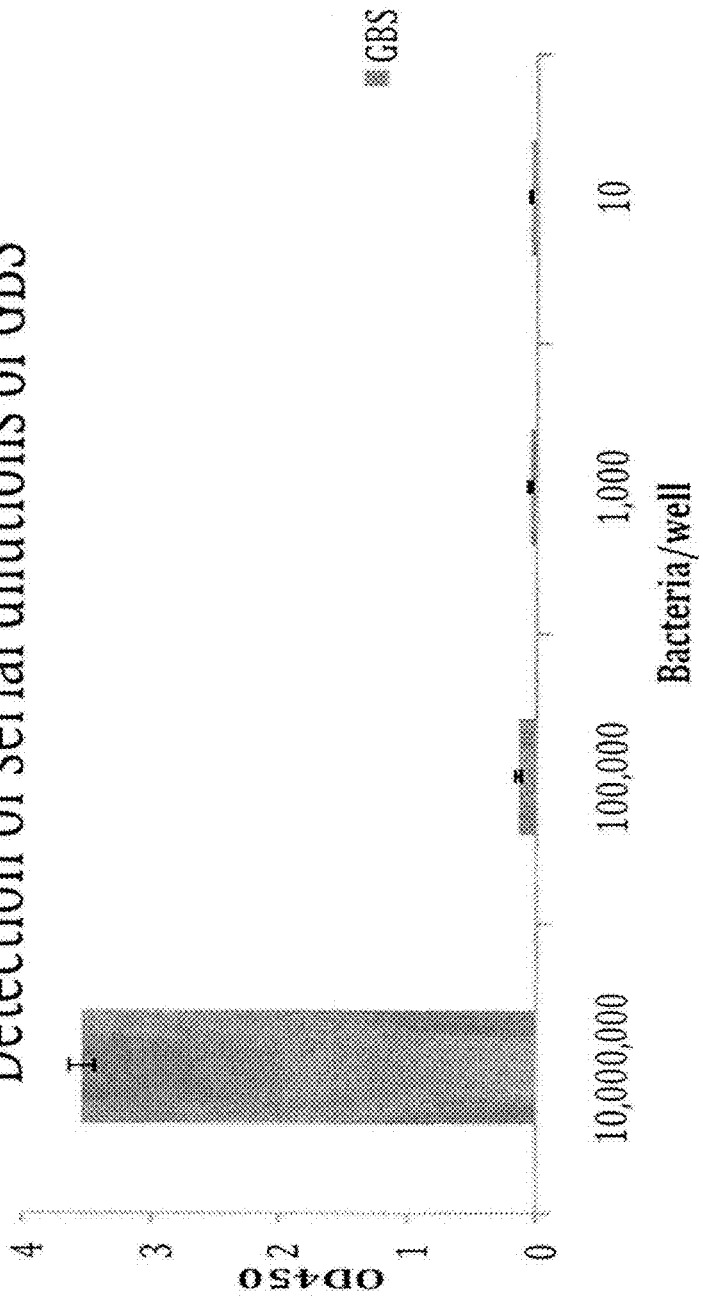
FIG. 1 is a bar graph showing detection of serial dilutions of GBS in wells coated with 1:60 dilution of polyclonal anti-GBS antibody, in accordance with invention.

The present invention provides a highly sensitive and specific enzyme-linked immunosorbent assay, referred to as N-Assay, for rapid detection and identification of a target microorganism in thirty minutes or less with little or no interference from non-target microorganisms. The present invention also provides for the simultaneous determination of antimicrobial susceptibility of the microorganism in the same assay in thirty minutes or less.

Through a modification of a recently reported test, the inventors have developed an assay, the N-Assay, for the simultaneous identification of a pathogen and determination of its antibiotic susceptibility. By substituting antibodies specific for certain pathogens, the inventors have modified the test so that GBS, *Enterococcus faecalis*, vancomycin-resistant *enterococcus* (VRE, i.e., *Enterococcus faecium*), and *Neisseria gonorrheae* may be detected in 30 minutes or less, or in cases in which more dilute bacterial load is present, results may be determined after an 18 to 24 hour incubation. The N-Assay also provides information regarding the pathogen's susceptibility to selected antibiotics, and thus may allow for a more targeted approach in treating infectious diseases.

Microorganisms that can be detected and identified in as little as 30 minutes or less using the methods of the present invention include, without limitation, bacteria, such as Group B *Streptococcus* (GBS) as well as Groups A, C, F and G *Streptococcus*, *Staphylococcus aureus*, *Neisseria gonorrheae*, *Enterococcus faecalis*, *Enterococcus faecium*, and *Escherichia coli*; fungi such as *Candida albicans* and *Pneumocystis pneumonia*, yeasts, molds and parasites.

In accordance with the invention, any number of serial dilutions of a microorganism may be prepared and assayed in accordance with the methods of the invention. In an embodiment, four serial dilutions of a microorganism may be prepared, ranging anywhere from $10^8$ to $10^1$ bacteria.

In an embodiment, the enzyme conjugated to an antibody is horseradish peroxidase (HRP) and the substrate specific to the enzyme is tetramethylbenzidine (TMB).

All available antimicrobials may be used in the methods of the invention to determine antimicrobial resistance of a target microorganism, such as, without limitation, antibiotics such as, without limitation, penicillin, clindamycin, vancomycin, cephalosporin, ceftriaxone, and many others currently known or to be discovered which exhibit antimicrobial action.

EXAMPLES

The present invention is more particularly described in the following non-limiting examples, which are intended to be illustrative only, as numerous modifications and variations therein will be apparent to those skilled in the art.

Examples 1, 3, and 5 provide investigations performed to identify GBS, *Neisseria gonorrhea* and *Enterococcus faecalis* using the rapid enzyme-linked immunosorbent assay of the invention, referred to herein as the "N-Assay". In Examples 2 and 4, investigations were performed to identify GBS and *Neisseria gonorrheae* and to simultaneously determine their susceptibility to specific antibiotics.

Example 6 provides an improved, modified rapid enzyme-linked immunosorbent assay (N-Assay) to identify, with very high specificity and sensitivity, four strains of bacteria: GBS, *Enterococcus faecalis, Enterococcus faecium* and *Neisseria gonorrheae* in about 30 minutes or less, and an assay to simultaneously identify these four strains of bacteria and determine their susceptibility to specific antibiotics in about 24 hours or less, a substantially shorter time than current state of the art protocols, which require at least 3 to 5 days, to determine microbial susceptibility to antibiotics.

Example 1

Detection of GBS

Methods

Two strains of GBS (GBS ATCC 12386 and patient isolates GBS 1.12.76) were cultured overnight on CNA agar. A 0.5 McFarland was prepared, and strains were diluted serially in phosphate-buffered saline (PBS) from $10^7$ to $10^1$. Microtiter wells were coated with 100 µl of a rabbit polyclonal antibody directed against GBS (VIROSTAT 1521) at specified dilutions, and allowed to stand at 4 degrees Celsius overnight. Additional antibodies directed against GBS which are commercially available were purchased and examined for their binding to GBS. Each of the additional antibodies (Pierce monoclonal antibodies and VIROSTAT monoclonal antibodies) was added to microtiter wells at specified dilutions, either alone or in the presence of the polyclonal anti-GBS antibody (VIROSTAT 1521). Wells were then washed three times with PBS, and subsequently blocked with 200 µl of 5% milk or STARTINGBLOCK (Pierce) at room temperature for 30 minutes. Following blocking, wells were again washed three times with PBS. Next, 100 µl of the selected GBS dilutions were placed in individual wells, and shaken gently on a plate stirrer at room temperature for 15 minutes. Next, wells were washed three times with PBS, and 100 µl of an HRP-conjugated rabbit polyclonal antibody (1:50 dilution in PBS) directed against GBS (VIROSTAT 1524) was added to the wells and incubated at room temperature for 5 minutes. Wells were washed three times with PBS, and then bound antibody was detected by the addition of 100 µl of tetramethylbenzidine (TMB) substrate. $OD_{450}$ was read after allowing the plate to stand for three minutes at room temperature and stopping the reaction with stop solution (KPL). Blank wells consisted of the same preceding steps, with the difference being that the step requiring the addition of bacteria was omitted. *Neisseria gonorrheae, Enterococcus faecalis,*

Groups A, C, F and G *streptococcus*, and *Staphylococcus aureus* were used as negative controls.

To reduce background binding observed when *S. aureus* was added to the GBS sample, the following approaches were undertaken: bacterial mixtures were incubated in the presence of Triclosan, wells were inoculated with bacterial mixtures after adding Protein A to the blocking step, or bacterial mixtures were first pre-incubated for a specified time in tubes coated with Fc-fragment. The remainder of the assay was performed as described above.

Results

Coating microtiter wells with 1:60 dilution of polyclonal anti-GBS antibody resulted in detection of GBS at a concentration of $10^7$ bacteria/well (FIG. 1). As the bacteria were diluted further, the signal generated by labeled antibody was increasingly diminished. This was tested with $10^7$ bacteria/well *Neisseria gonorrheae*, and binding of HRP-conjugated anti-GBS antibody to *Neisseria gonorrheae* was not observed (data not shown).

Figure 2:
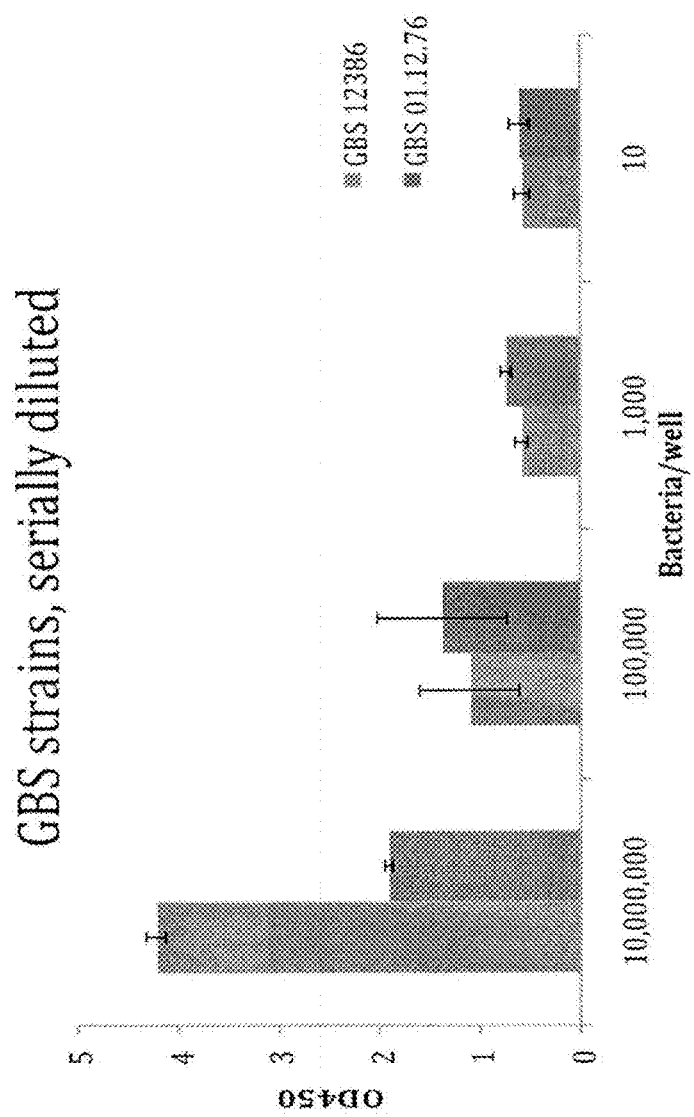
FIG. 2 is a bar graph showing detection of serial dilutions of GBS in wells coated with 1:15 dilution of polyclonal anti-GBS antibody, in accordance with invention.

Plates were next prepared with coating antibody concentrations of 1:50, 1:30 and 1:15, diluted in coating buffer. Binding of GBS to coating antibody was significantly increased when concentrations of coating antibody was increased. FIG. 2 shows that a coating dilution of 1:15 allowed for the detection of GBS at a concentration as dilute as $10^1$ bacteria/well. Both the ATCC strain and the clinical isolate strain showed positive signal at all dilutions tested. All results were obtained in about 30 minutes from the time the GBS strains were added to the wells.

Figure 3:
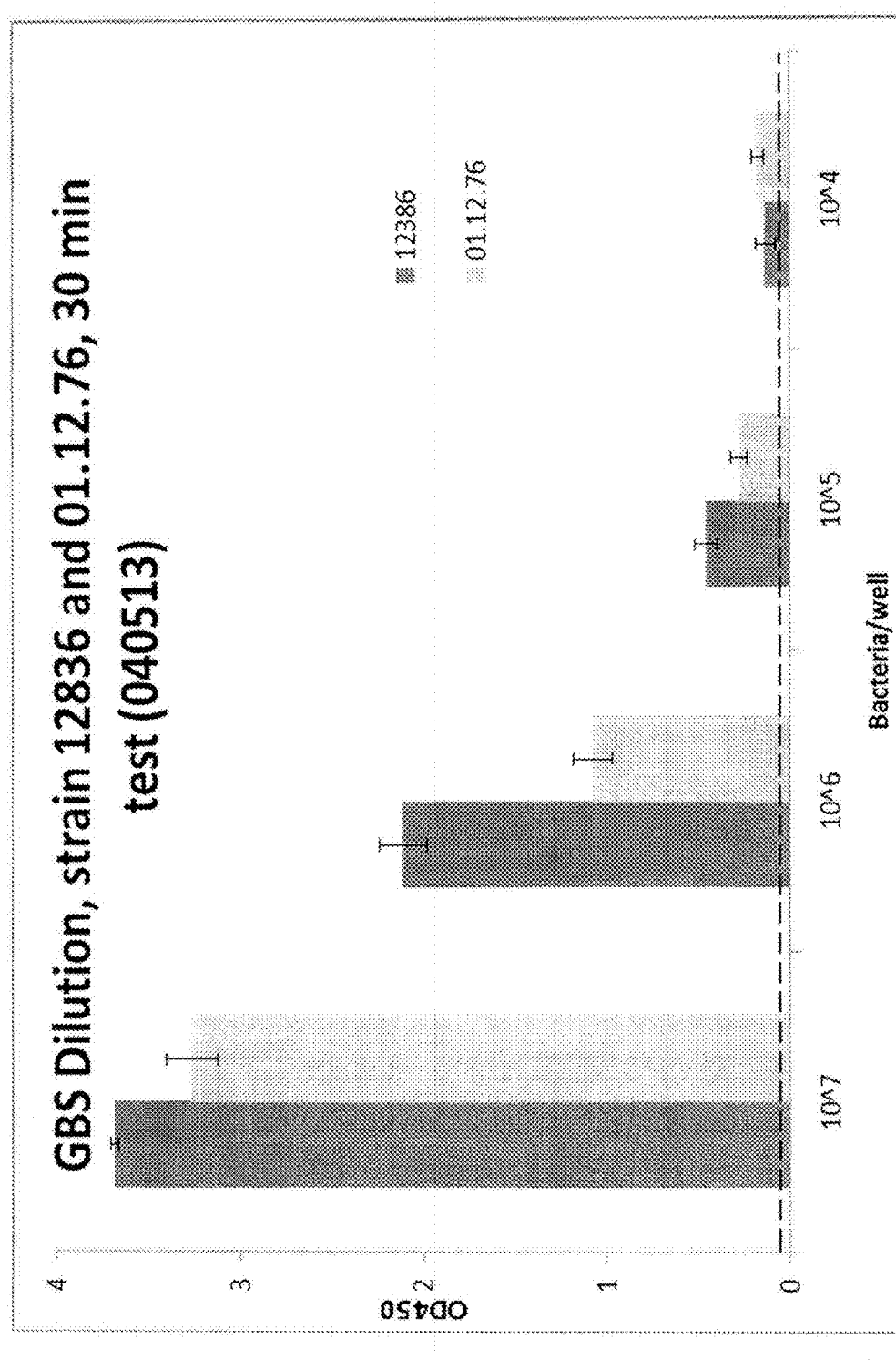
FIG. 3 is a bar graph showing detection of serial dilutions of two strains of GBS coated with 1:30 polyclonal antibodies, 1:50 VIROSTAT monoclonal antibodies; and 1:500 Pierce monoclonal antibodies, in accordance with the invention.

In order to increase the sensitivity of the assay, additional monoclonal antibodies directed against GBS were added to the coating step. Each monoclonal antibody was studied individually at the following dilutions: Pierce monoclonal antibody 1:50, 1:100, 1:250, 1:500 and 1:1000; and VIROSTAT monoclonal antibody 1:50, 1:100, 1:250, 1:500 and 1:1,000. Once binding was optimized, the antibody dilutions were mixed and a GBS curve was generated (not shown). The use of 1:30 polyclonal antibody, 1:50 VIROSTAT monoclonal antibody, and 1:500 Pierce monoclonal antibody allowed for detection of both the ATCC strain and the clinical isolate strain of GBS from $10^7$ to $10^4$ bacteria/well in 30 minutes or less (FIG. 3).

Figure 4:
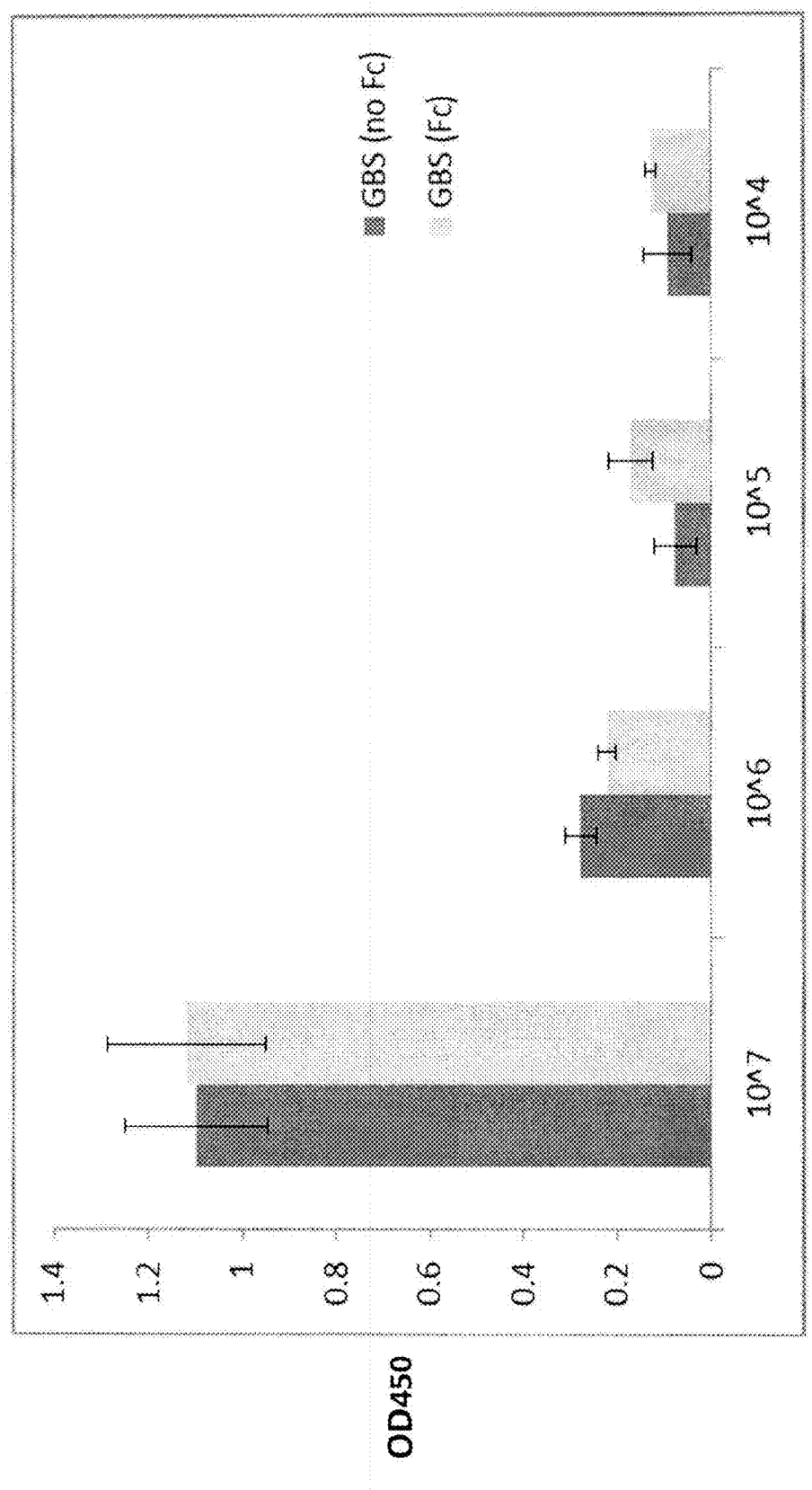
FIG. 4 is a bar graph showing the effect of pre-incubation of GBS with Fc-fragments on detection of serial dilutions of GBS, in accordance with the invention.

Pre-incubation of GBS with Fc-fragments did not significantly affect GBS binding to coating antibody or detection times (FIG. 4).

Figure 5:
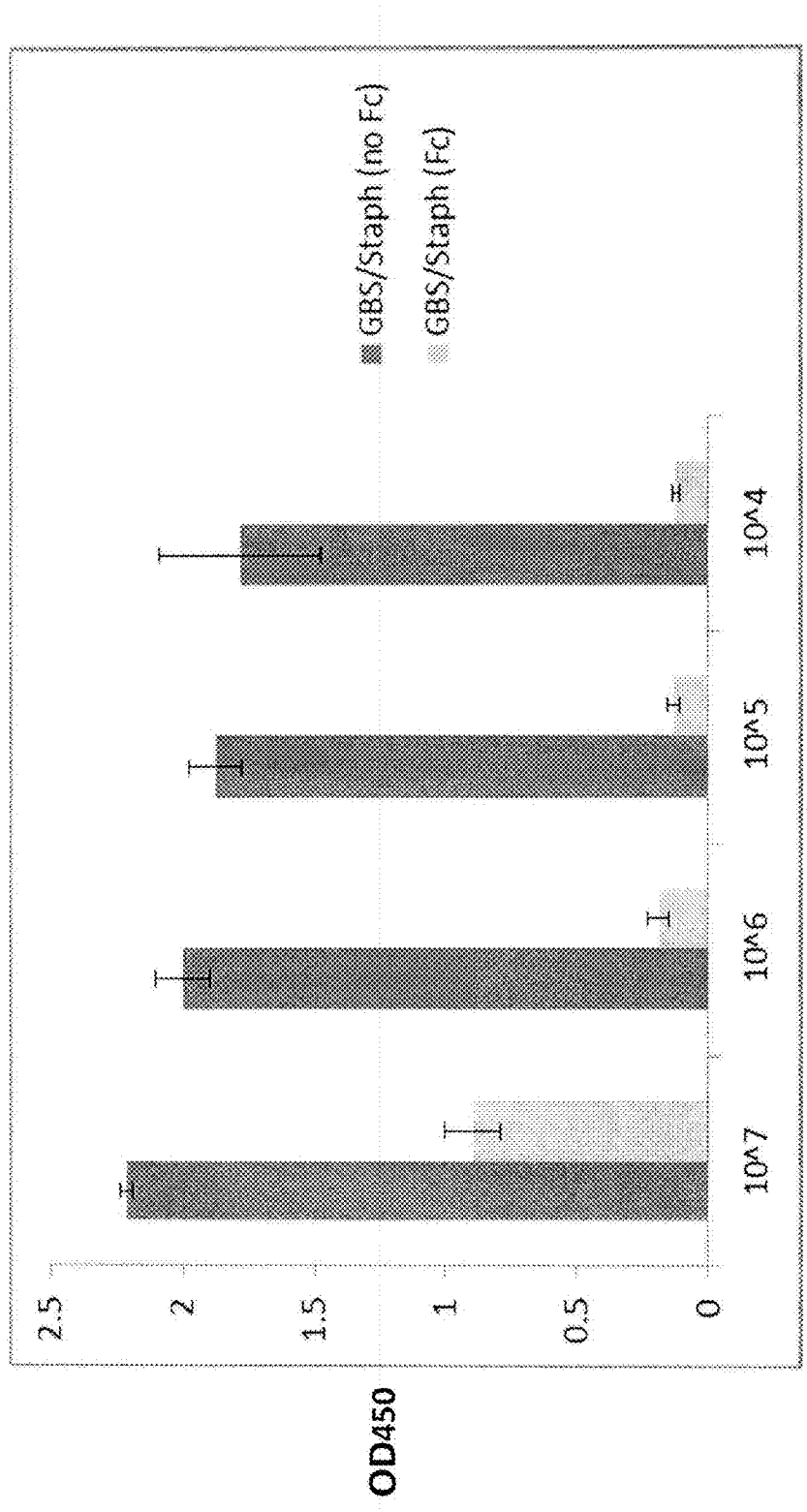
FIG. 5 is a bar graph showing the effect of pre-incubation of GBS with Fc-fragments on binding interference of *S. aureus* when mixtures of GBS and *S. aureus* are inoculated in wells, in accordance with the invention.
Figure 6:
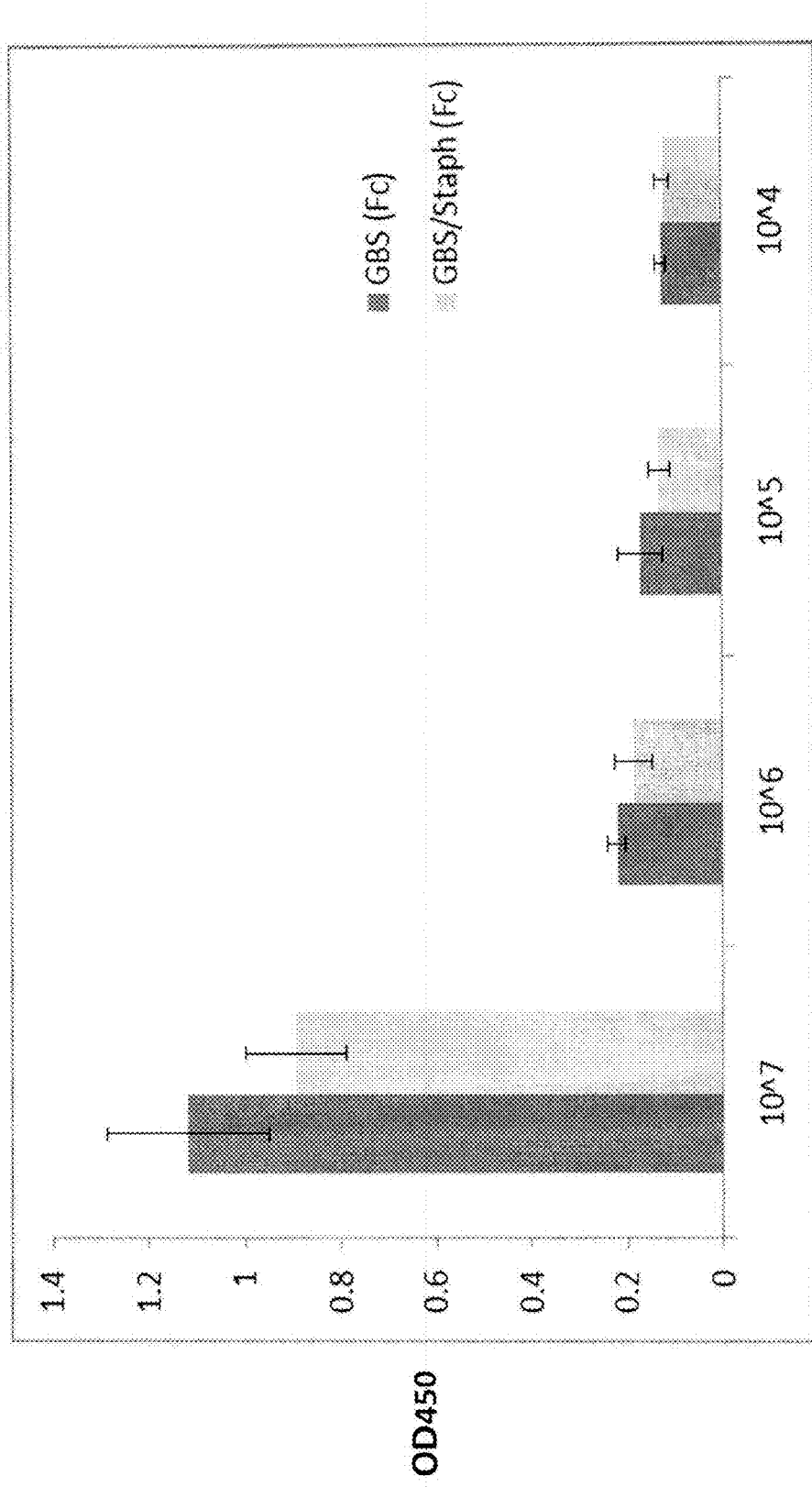
FIG. 6 is a bar graph showing pre-incubation of GBS with Fc-fragments on binding interference by *S. aureus*, in accordance with the invention.

Pre-incubation of GBS with Fc-fragments eliminated binding interference of *S. aureus* when mixtures of GBS and *S. aureus* were inoculated in wells. Dilutions of $10^7$ to $10^4$ GBS/well were used, while *S. aureus* was held constant at $10^7$/well (FIG. 5). FIG. 6 shows that pre-incubating GBS with Fc-fragments eliminated binding interference by *S. aureus*.

Example 2

Simultaneous Identification of GBS and Determination of Antimicrobial Susceptibility Methods Two strains of GBS (GBS ATCC 12386 and patient isolates GBS 1.12.76) were cultured overnight on CNA agar. A 0.5 McFarland was prepared immediately before wells were to be inoculated, and strains were diluted serially in LIM broth from $10^7$ to $10^2$. Microtiter wells were coated with 100 µl of a 1:15 dilution of rabbit polyclonal antibody directed against GBS (VIROSTAT 1521), and allowed to stand at 4 degrees Celsius overnight. Wells were then washed three times with PBS, and subsequently blocked with 200 µl STARTING-BLOCK (Pierce) at room temperature. Following blocking, wells were again washed three times with PBS. At this stage, the plates were either used immediately, or stored at 4 degrees Celsius for later use. Upon proceeding with the assay, 100 µl of the selected GBS dilutions were placed in individual wells, and shaken gently on a plate stirrer at room temperature for 15 minutes. Next, wells were washed three times with PBS, and 100 µl of an HRP-conjugated rabbit polyclonal antibody (1:50 dilution in PBS) directed against GBS (VIROSTAT 1524) was added to the wells and incubated at room temperature for 5 minutes. Wells were washed three times with PBS, and then bound antibody was detected by the addition of 100 µl of TMB substrate. $OD_{450}$ was read after allowing the plate to stand for 3 minutes at room temperature and stopping the reaction with stop solution (KPL). Negative controls consisted of the same preceding steps, but the addition of bacteria was omitted.

In order to determine antimicrobial susceptibility, clindamycin was added to wells inoculated with varying concentrations of GBS. The breakpoint of clindamycin for GBS resistance has been shown to be 2 µg/ml. Therefore, two concentrations of clindamycin were used in this assay. Wells were inoculated with serial dilutions of 100 µl of GBS in LIM broth, and to each well was added either 0.2 µg/ml or 2.0 µg/ml of clindamycin. As a negative control, buffer alone was added. The experiment was continued as described above, so that after a 20-minute incubation at room temperature, wells were washed and then HRP-conjugated antibody was added and bound GBS was detected by $OD_{450}$.

Results

Both the ATCC strain and the clinical isolate strain showed positive signal at dilutions tested in the negative control wells and wells containing 0.2 µg/ml of clindamycin. In the wells containing 2.0 µg/ml of clindamycin, the signal was greatly diminished, showing the antimicrobial susceptibility of both GBS strains to this antimicrobial agent. All results were obtained in less than 30 minutes from the time the GBS strains were added to the wells.

Example 3

Detection of *Neisseria gonorrheae*

Methods

*N. gonorrheae* was cultured overnight on gonococci (Gc) agar. A 0.5 McFarland was prepared immediately before wells were to be inoculated, and strains were diluted serially in fastidious broth (FB) from $10^8$ to $10^2$. Microtiter wells were coated with 100 µl of a rabbit polyclonal antibody directed against *N. gonorrheae* at two dilutions: 1:200 and 1:100, and allowed to stand at 4 degrees Celsius overnight. Wells then were washed three times with PBS, and subsequently blocked with 200 µl 5% milk at room temperature for 20 minutes. Following blocking, wells were again washed three times with PBS. At this stage, the plates were either used immediately, or stored at 4 degrees Celsius for later use. Upon proceeding with the assay, 100 µl of the selected *N. gonorrheae* dilutions were placed in individual wells, and shaken gently on a plate stirrer at room temperature for 15 minutes. Next, wells were washed three times with PBS, and 100 µl of an HRP-conjugated rabbit polyclonal antibody (1:50 dilution in PBS) directed against *N. gonorrheae* was added to the wells and incubated at room temperature for 5 minutes. Wells were washed three times with PBS, and then bound antibody was detected by the addition of 100 µl of TMB substrate. $OD_{450}$) was read after allowing the plate to stand for 3 minutes at room temperature and stopping the reaction with stop solution (KPL). Negative controls consisted of the same preceding steps, but the addition of bacteria was omitted.
Results
Coating microtiter wells with both dilutions of polyclonal anti-gonorrheal antibody resulted in a positive signal at all dilutions tested. Strong detection of *N. gonorrheae* was seen at a concentration of $10^8$ bacteria/well, with good detection at a concentration of $10^6$ bacteria/well. At concentrations of $10^4$ and $10^2$ bacteria/well, the signal generated by labeled antibody was substantially diminished but still positive. Results were obtained in less than 30 minutes from the time the bacteria was added to the wells.

Example 4

Simultaneous Identification of *Neisseria gonorrheae* and Determination of Antimicrobial Susceptibility Methods
Two strains of *N. gonorrheae*, penicillin-sensitive (Pen-S) Strain 1279 and penicillin-resistant (Pen-R) Strain 31426, were cultured overnight on Gc agar. A 0.5 McFarland was prepared immediately before wells were to be inoculated, and the two strains were each diluted to a concentration of $10^8$ in FB. The bacteria-containing FB for each strain was split into four tubes, in which a different concentration of penicillin was added to each of the tubes of the two strains: 2.0 μg/ml, 1.0 μg/ml, 0.5 μg/ml, and buffer alone as a negative control. Microtiter wells were coated with 100 μl of a 1:200 dilution of rabbit polyclonal antibody directed against *N. gonorrheae*, and allowed to stand at 4 degrees Celsius overnight. Wells were then washed three times with PBS, and subsequently blocked with 5% milk at room temperature for 20 minutes. Following blocking, wells were again washed three times with PBS. At this stage, the plates were either used immediately, or stored at 4 degrees Celsius for later use. Upon proceeding with the assay, 100 μl of the $10^8$ dilution of the two strains of *N. gonorrheae* were placed in individual wells. The wells were shaken gently on a plate stirrer at room temperature for 15 minutes. Next, wells were washed three times with PBS, and 100 μl of an HRP-conjugated rabbit polyclonal antibody (1:50 dilution in PBS) directed against *N. gonorrheae* was added to the wells and incubated at room temperature for 5 minutes. Wells were washed three times with PBS, and then bound antibody was detected by the addition of 100 μl of TMB substrate. $OD_{450}$ was read after allowing the plate to stand for three minutes at room temperature and stopping the reaction with stop solution (KPL). Negative controls consisted of the same preceding steps, but the addition of bacteria was omitted.
Results
Pen-S Strain 1279 showed a progressively decreasing positive signal with the increasing concentrations of penicillin. In contrast, Pen-R Strain 31426 showed a positive signal that did not significantly vary between any of the concentrations of penicillin. Growth was confirmed by detecting increasing turbidity at $OD_{600}$ in wells containing Pen-R strain 31426. Results were obtained in less than 30 minutes from the time the two strains of *N. gonorrheae* were added to the wells.

Example 5

Detection of *Enterococcus Faecalis*

Methods
*E. faecalis* was cultured overnight on CNA agar. A 0.5 McFarland was prepared immediately before wells were to be inoculated, and strains were diluted serially in PBS from $10^8$ to $10^2$. Microtiter wells were coated with 100 μl of a rabbit polyclonal antibody directed against *E. faecalis* at two dilutions: 1:200 and 1:100, and allowed to stand at 4 degrees Celsius overnight. Wells were then washed three times with PBS, and subsequently blocked with 200 μl 5% milk at room temperature for 20 minutes. Following blocking, wells were again washed three times with PBS. At this stage, the plates were either used immediately, or stored at 4 degrees Celsius for later use. Upon proceeding with the assay, 100 μl of the selected *E. faecalis* dilutions were placed in individual wells, and shaken gently on a plate stirrer at room temperature for 15 minutes. Next, wells were washed three times with PBS, and 100 μl of an HRP-conjugated rabbit polyclonal antibody (1:100 dilution in PBS) directed against *E. faecalis* was added to the wells and incubated at room temperature for 7 minutes. Wells were washed three times with PBS, and then bound antibody was detected by the addition of 100 μl of TMB substrate. $OD_{450}$ was read after allowing the plate to stand for 3 minutes at room temperature and stopping the reaction with stop solution (KPL). Negative controls consisted of the same preceding steps, but the addition of bacteria was omitted.
Results
Coating microtiter wells with both dilutions of polyclonal anti-faecalis antibody resulted in a positive signal at all dilutions tested. Strong detection of *E. faecalis* was seen at a concentration of $10^8$ bacteria/well. At concentrations of $10^6$, $10^4$ and $10^2$ bacteria/well, the signal generated by labeled antibody was substantially diminished but still positive. Growth was confirmed by detecting increasing turbidity at $OD_{600}$ in wells containing Pen-R strain 31426. Results were obtained in less than 30 minutes from the time the bacteria was added to the wells.

Example 6

Figure 7:
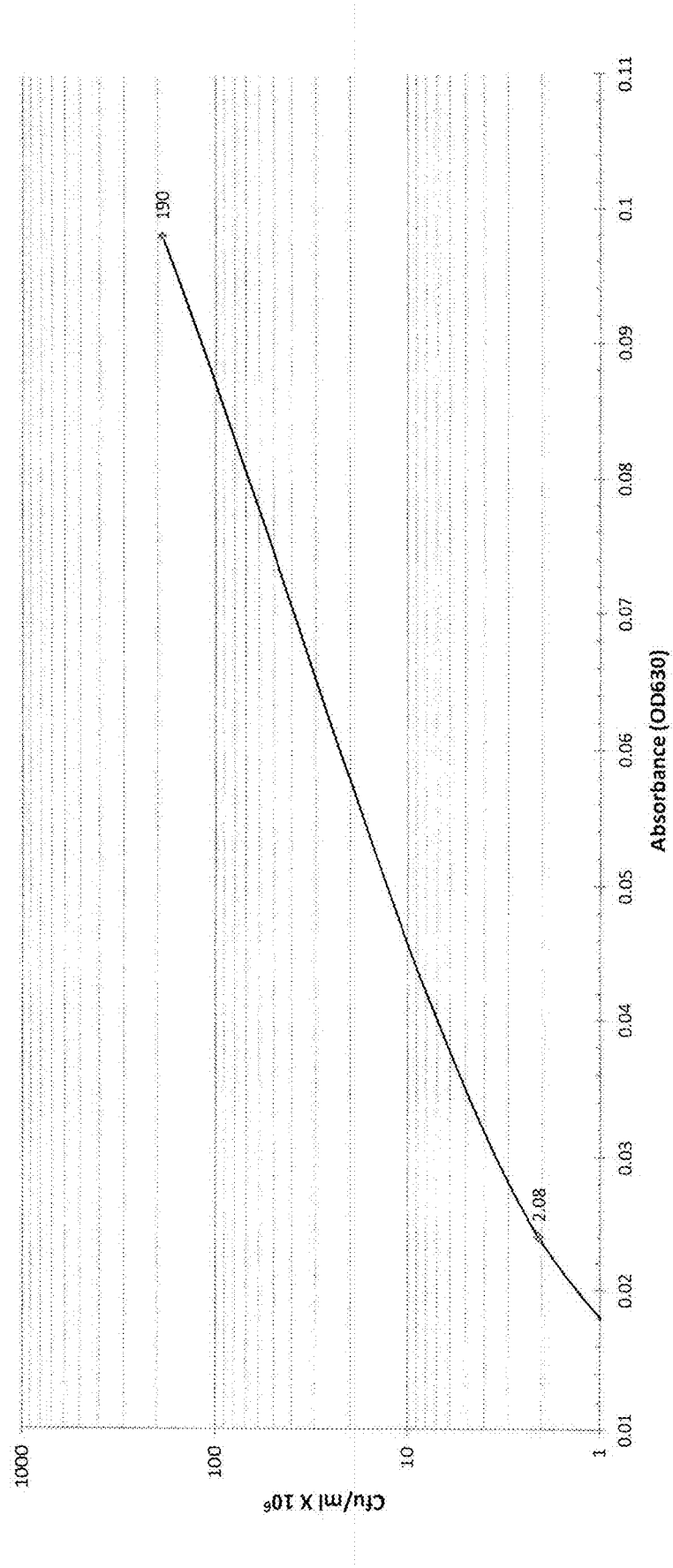
FIG. 7 is a dilution curve of *N. gonorrhea* colony-forming units (CFU) at various dilutions plotted on a semi-log graph, in accordance with the invention.
Figure 8:
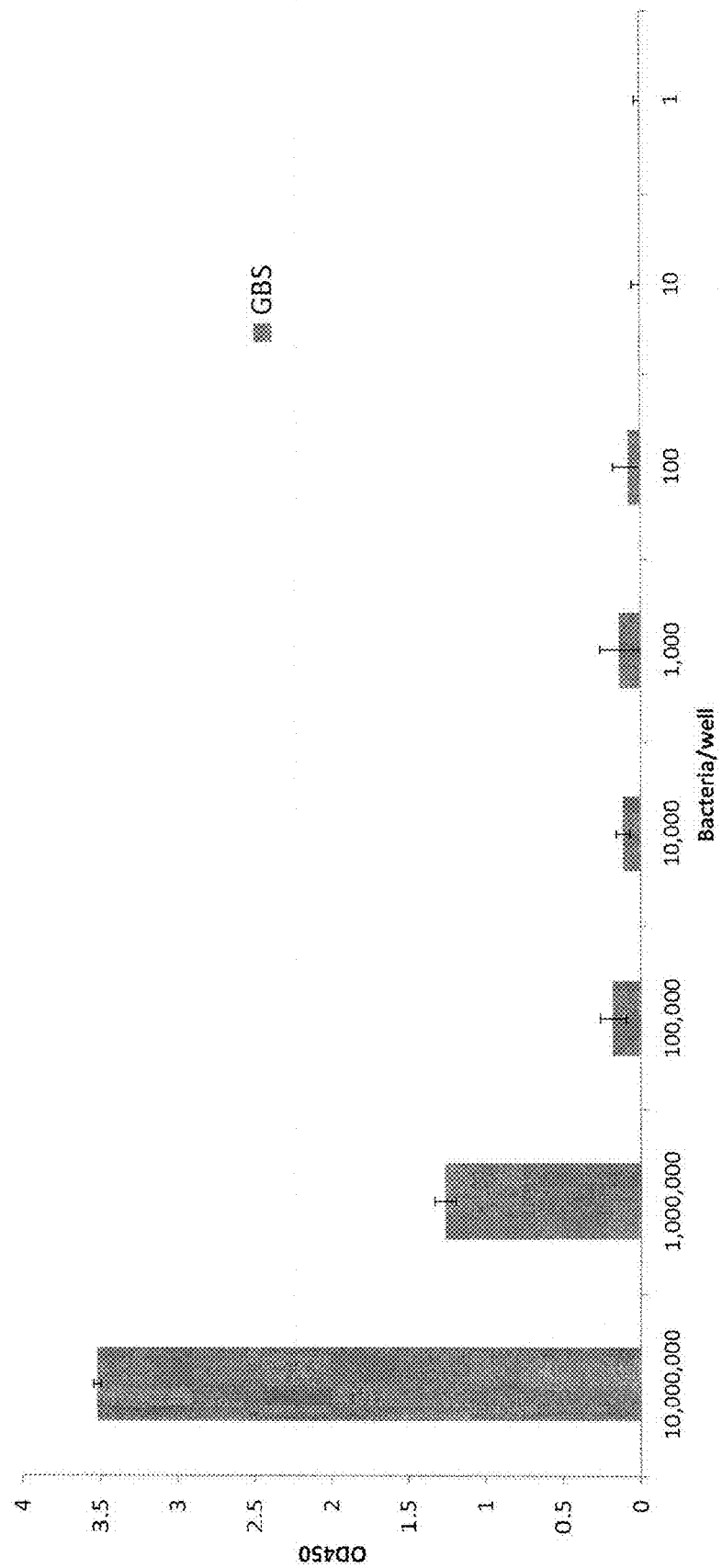
FIG. 8 is a bar graph showing detection of GBS by the rapid N-Assay after a 15 minute incubation, in accordance with the invention.
Figure 9:
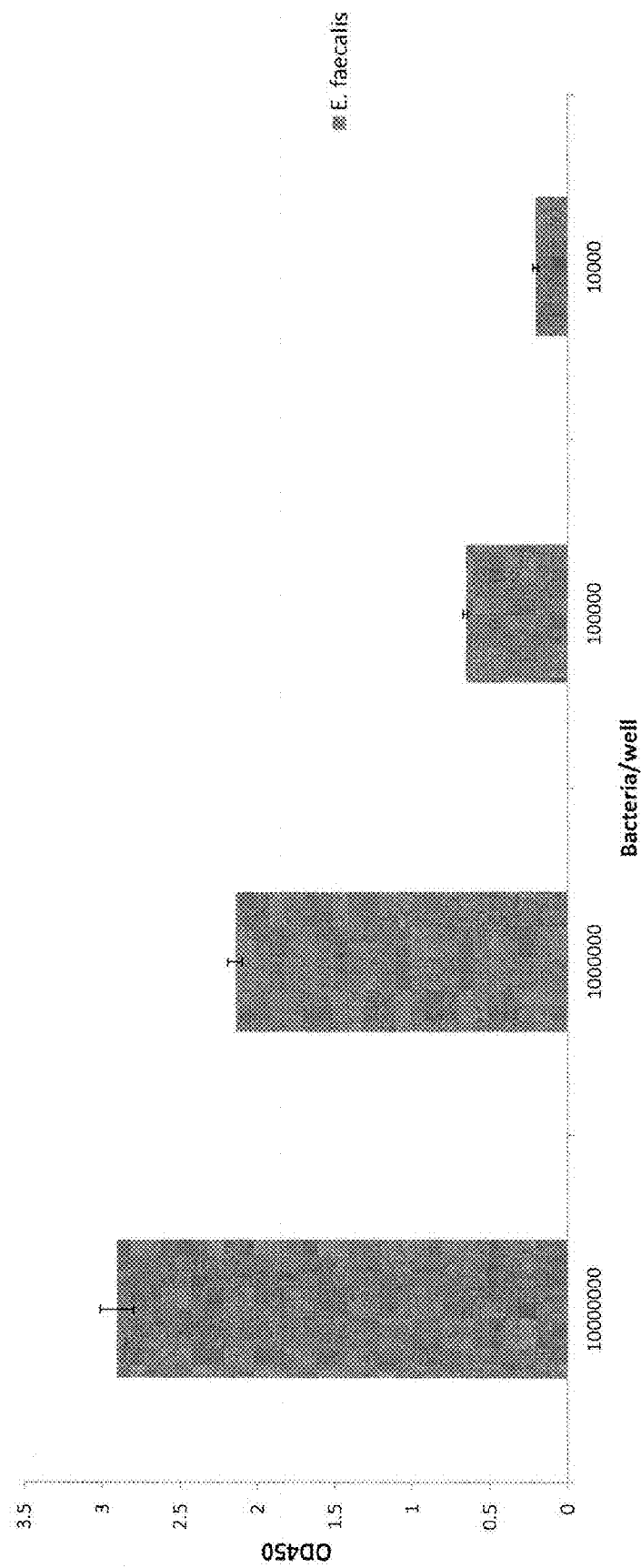
FIG. 9 is a bar graph showing detection of *E. faecalis* by the rapid N-Assay after a 15 minute incubation, in accordance with the invention.
Figure 10:
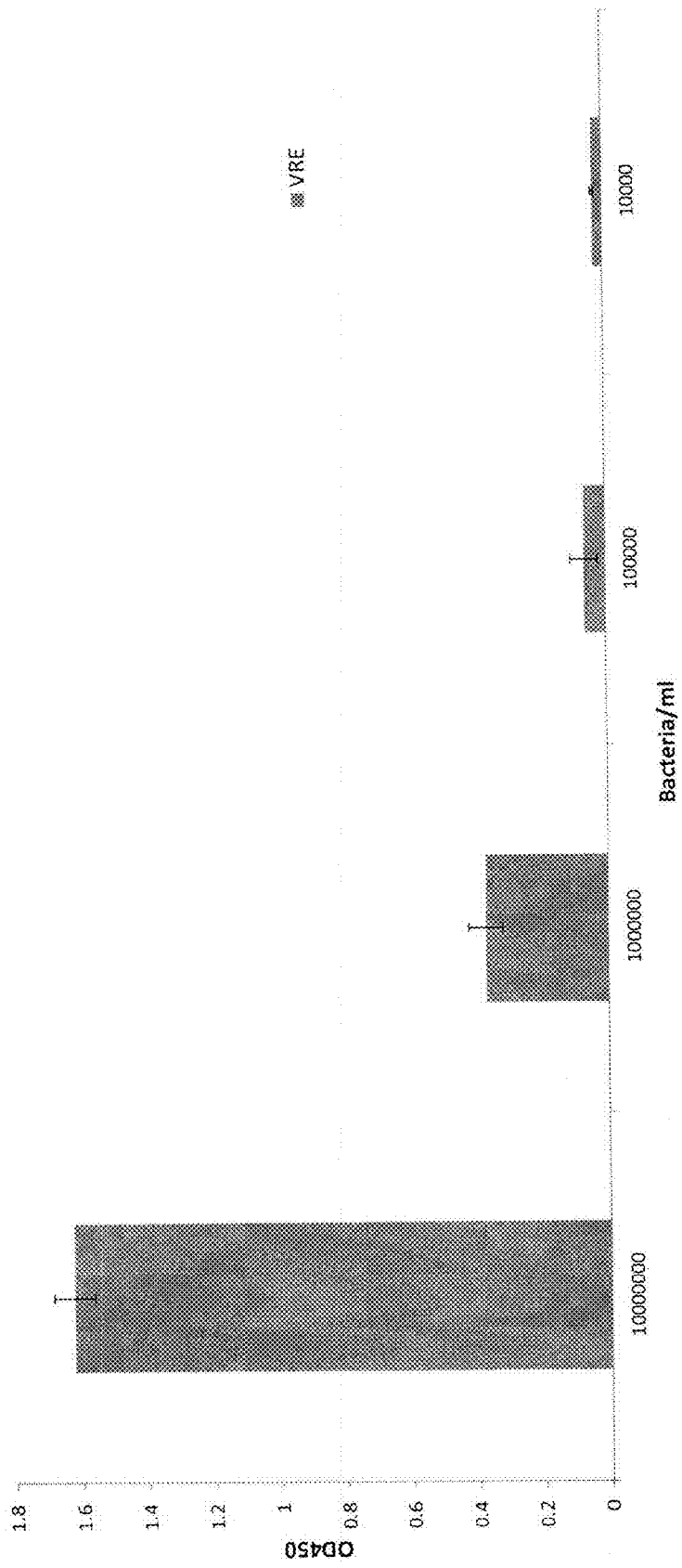
FIG. 10 is a bar graph showing detection of *E. faecium* (Vancomycin-Resistant *Enterococcus*) by the rapid N-Assay after a 15 minute incubation, in accordance with the invention.
Figure 11:
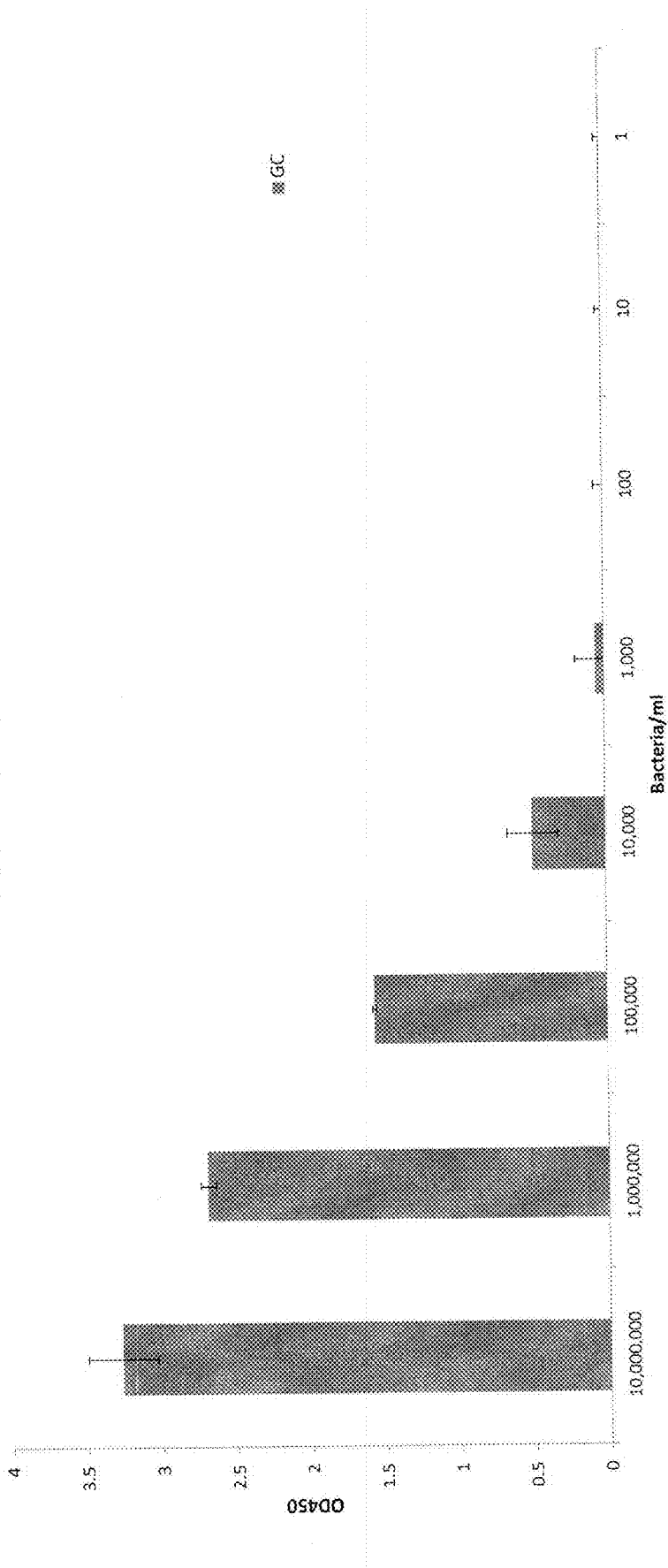
FIG. 11 is a bar graph showing detection of *N. gonorrheae* by the rapid N-Assay after a 15 minute incubation, in accordance with the invention.

Simultaneous Identification of Four Strains of Bacteria and Determination of Their Antibiotic Susceptibility Methods
Reagents
Microtiter plates were purchased from Nunc (Immulon 4HBK 96 well plate) or Corning (Costar 3590 96 well plate).
Carbonate-bicarbonate buffer was purchased from Sigma Aldrich (C3041) and diluted 1:100 prior to use. PBS tablets were purchased from Sigma Aldrich (P4417) and buffer was prepared prior to use. TWEEN 20 was purchased from Fisher Scientific (9005-64-C58H114026). STARTINGBLOCK was purchased from ThermoScientific (37538). TMB and Stop solution were purchased from ThermoScientific (34012).
Antibodies were purchased from Fisher Scientific (non-conjugated anti-gonorrhea antibody PA1-7233, and HRP-conjugated anti-gonorrhea antibody PA1-73144) and VIROSTAT (non-conjugated anti-GBS antibody 1521, HRP-conjugated anti-GBS antibody 1524, non-conjugated anti-Enterococcus antibody 3711 and HRP-conjugated anti-Enterococcus antibody 3714).
Antibiotics studied included ceftriaxone, clindamycin, and penicillin G. The clindamycin (C5269) and penicillin G (P3032) were both purchased from Sigma Aldrich, and the ceftriaxone (104376-79-6) was purchased from TCI Chemicals.
Bacteria studied included *Enterococcus faecalis* (ATCC 29212), *Enterococcus faecium* (ATCC 700221), GBS (clinical isolate 01.12.76, shown to be resistant to clindamycin; and isolate 198, shown to be sensitive to clindamycin), and *Neisseria gonorrhea* (ATCC 31426, beta-lactamase positive).
Preparation of Bacteria Prior to performing the N-Assay, bacterial cultures were prepared as follows in order to establish the sensitivity of the assay. An inoculum was taken from a stock culture, and plated onto solid phase nutrient agar and incubated overnight at 37° C. *E. faecalis, E. faecium* (Vancomycin-Resistant *Enterococcus*, or VRE) and GBS isolates were plated onto colistin and naladixic acid agar, and *N. gonorrheae* was plated onto chocolate agar. The gonorrheal culture was performed in a $CO_2$ incubator. Following an overnight culture, an isolated colony was selected of each bacterial species, and the isolated colonies were sub-cultured on solid phase for an additional 24 hours to ensure adequate viability was maintained. Following this, isolated cultures were used to inoculate nutrient broth (LIM broth was used for GBS, Fastidious broth with isovitalex 2% v/v for *N. gonorrheae*, and BHI broth was used for *E. faecalis, E. faecium*). A 0.5 McFarland was prepared for each bacterial species, and these were then diluted serially down to $10^{-3}$ in nutrient broth and the $OD_{630}$ immediately was determined. For each dilution, aliquots were obtained and agar plates were inoculated. The agar plates then were incubated at 37° C. for 24 hours, and the number of colony forming units (CFU) was determined for each bacterial species at each dilution. This was used to generate a standard curve, so that future dilutions when prepared could be developed with known concentrations of bacteria. FIG. 7 shows a representative dilution curve of the bacteria *Neisseria gonorrheae* and corresponding colony forming units (CFU) per ml. A similar curve was generated for each bacteria studied.
Rapid Enzyme Linked Immunosorbent Assay (ELISA/N-Assay)

Antibodies against selected bacteria were diluted 1:100 in coating buffer (carbonate bicarbonate buffer), and 100 μl were placed in microtiter wells and allowed to stand overnight at 4° C. The following day, wells were washed with PBS TWEEN 20 three times, and then blocked with 200 μl of STARTINGBLOCK for 30 minutes at room temperature. Following blocking, wells were washed three times with PBS TWEEN 20, and plates were either stored at 4° C. with a sterile cover placed over them for later use, or used immediately.

Performance of the assay included diluting the bacterial strains in PBS and placing the diluted suspensions in specified wells at a volume of 100 μl per well. The wells were allowed to stand at room temperature for 15 minutes, and wells then were washed three times with PBS TWEEN 2020. HRP-conjugated antibodies, each specific for a specific bacterial strain and diluted 1:100 in PBS, then was added at a volume of 100 μl per well, and wells were allowed to stand for 7 minutes at room temperature. The wells then were washed three times with PBS TWEEN 20, and TMB was added for three minutes at room temperature. Twenty-five μ of stop solution was added per well, and the $OD_{450}$ was determined. Positive signal was determined by a positive OD as compared to wells that had been blanked by the addition of non-specific bacteria (e.g., *Staphylococcus aureus* at $10^8$ bacteria/well). Alternatively, wells were determined to be positive if they turned yellow after addition of the stop solution, if a plate reader was not available.
Rapid Enzyme Linked Immunosorbent Assay (N-Assay) for Simultaneous Identification of Bacteria and Determination of Susceptibility to Antibiotics To determine antibiotic susceptibility of the four strains of bacteria, a 0.5 Mcfarland was prepared in nutrient broth and serially dilutions were established. The dilutions were incubated overnight for 18-24 hours at 37° C. (in a $CO_2$ incubator for *N. gonorrheae*) with specific antibiotics. Parallel dilutions were prepared of each bacterium, in the presence and absence of specific antibiotics, as follows: (1) for *E. faecalis, E. faecium*, Penicillin G was added in varying concentrations, and as these concentrations were held constant, the bacterial concentration was diluted out; (2) the same parameters were set for GBS with the antibiotic clindamycin; and (3) the same parameters were set for *N. gonorrheae* with the antibiotic ceftriaxone.

Following overnight incubation in the presence or absence of the selected antibiotics, 100 μl of the bacterial suspensions were placed into previously coated wells, and plates were allowed to stand at room temperature for 15 minutes. After washing with PBS TWEEN 20 three times, 100 μl of HRP-conjugated antibody directed against the specific bacteria was added in a 1:100 dilution, and allowed to stand at room temperature for 7 minutes. Wells were washed three times with PBS TWEEN 20, and bound antibody was detected by the addition of 100 μl of TMB substrate. $OD_{450}$) was read after allowing the plate to stand for 3 minutes at room temperature and stopping the reaction with stop solution (KPL).

After adding stop solution, wells were read at $OD_{450}$. Positive signal was determined by a positive OD as compared to wells that had been blanked by the addition of non-specific bacteria (e.g., *Staphylococcus aureus* at $10^8$ bacteria/well). Alternatively, wells were determined to be positive if they turned yellow after addition of the stop solution, if a plate reader was not available.
Results
Thirty Minute N-Assay: Identification of Bacterial Isolates Microtiter wells were inoculated with dilutions of the specific bacterial isolates GBS, *E. faecalis, E. faecium* and *N. gonorrheae*. Each bacterial isolate were detected in the range of $10^5$ bacteria/ml after a 15-minute incubation (FIGS. 8-11).

Figure 12:
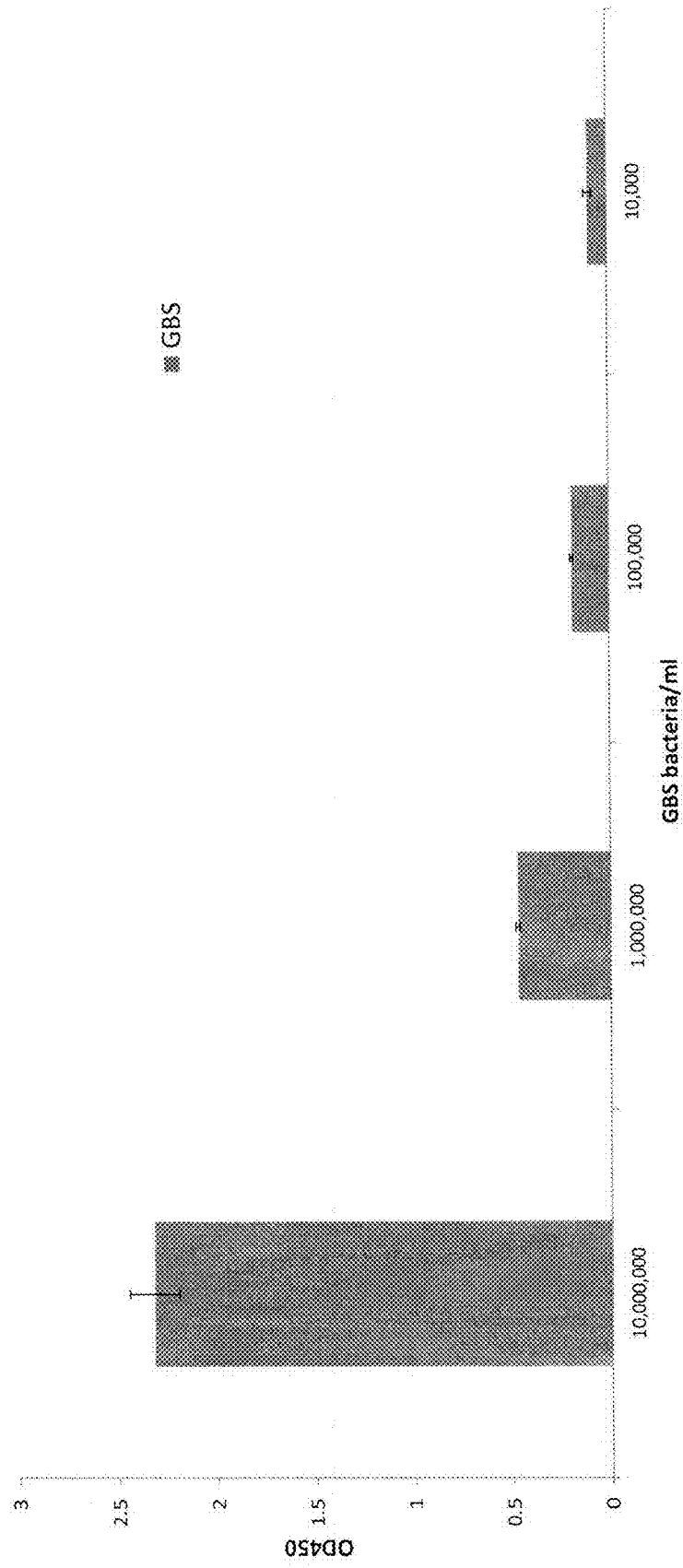
FIG. 12 is a bar graph showing the detection of GBS in serial dilutions with a competing organism, *C. albicans* held constant at $10^8$ fungi/ml to show specificity of the N-Assay, in accordance with the invention.
Figure 13:
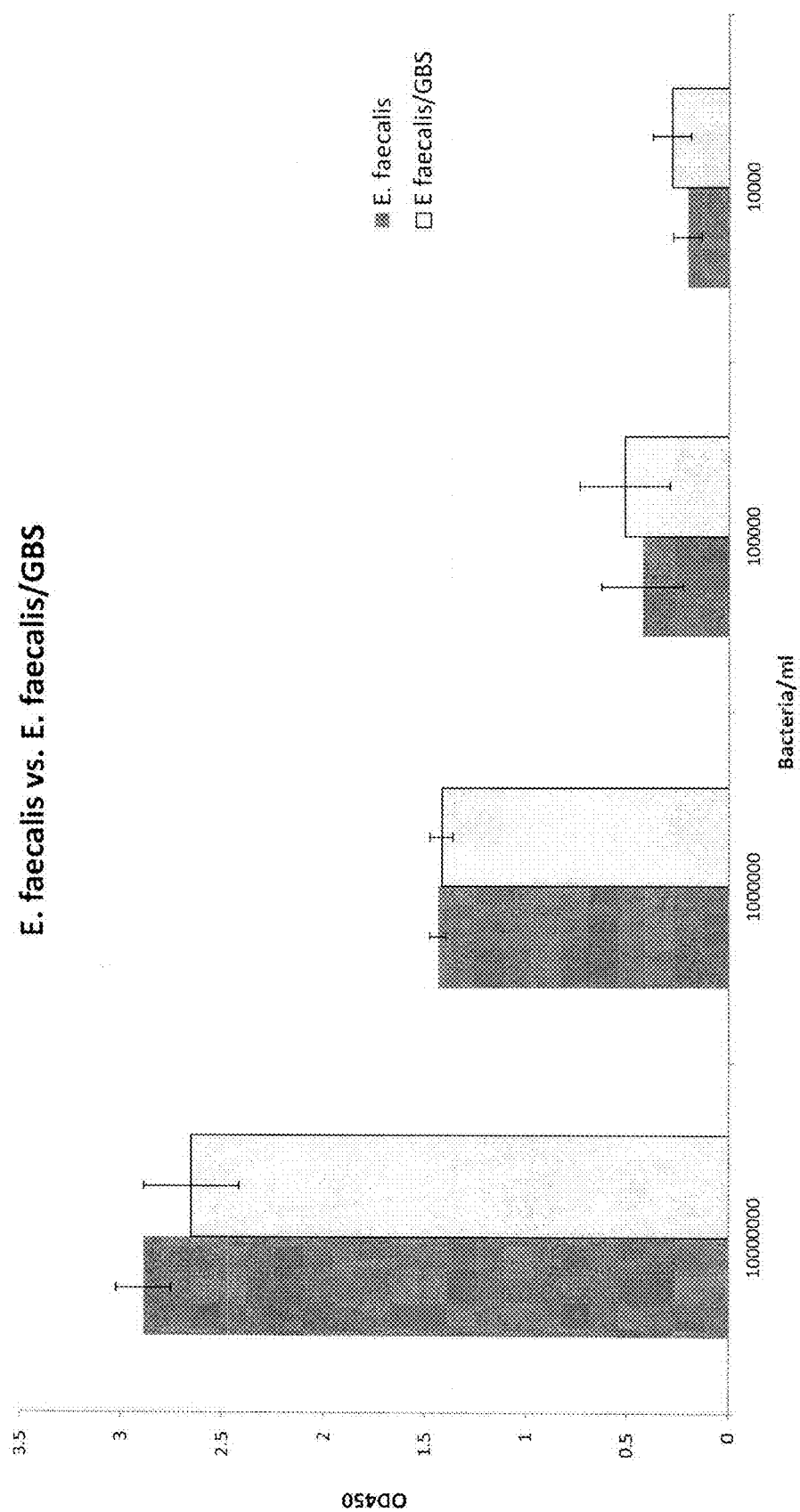
FIG. 13 is a bar showing the detection of *E. faecalis* in serial dilutions alone vs. *E. faecalis* with GBS as the competing organism, GBS held constant at $10^8$ bacteria/ml to show specificity of the N-Assay, in accordance with the invention.
Figure 14:
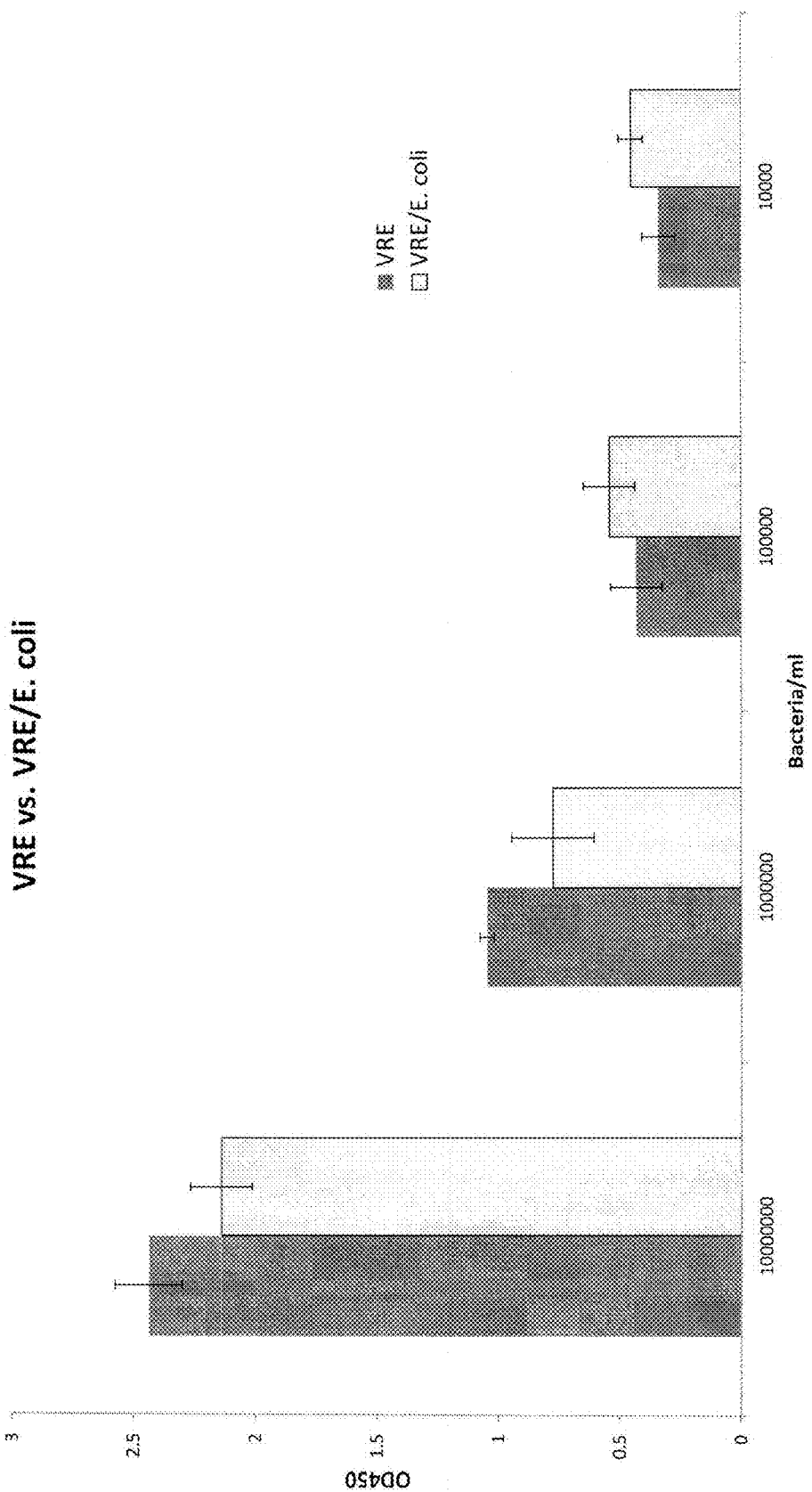
FIG. 14 is a bar showing the detection of *E. faecium* (Vancomycin-Resistant *Enterococcus*) in serial dilutions alone vs. *E. faecalis* with *E. coli* as the competing organism, *E. coli* held constant at $10^8$ bacteria/ml to show specificity of the N-Assay, in accordance with the invention.
Figure 15:
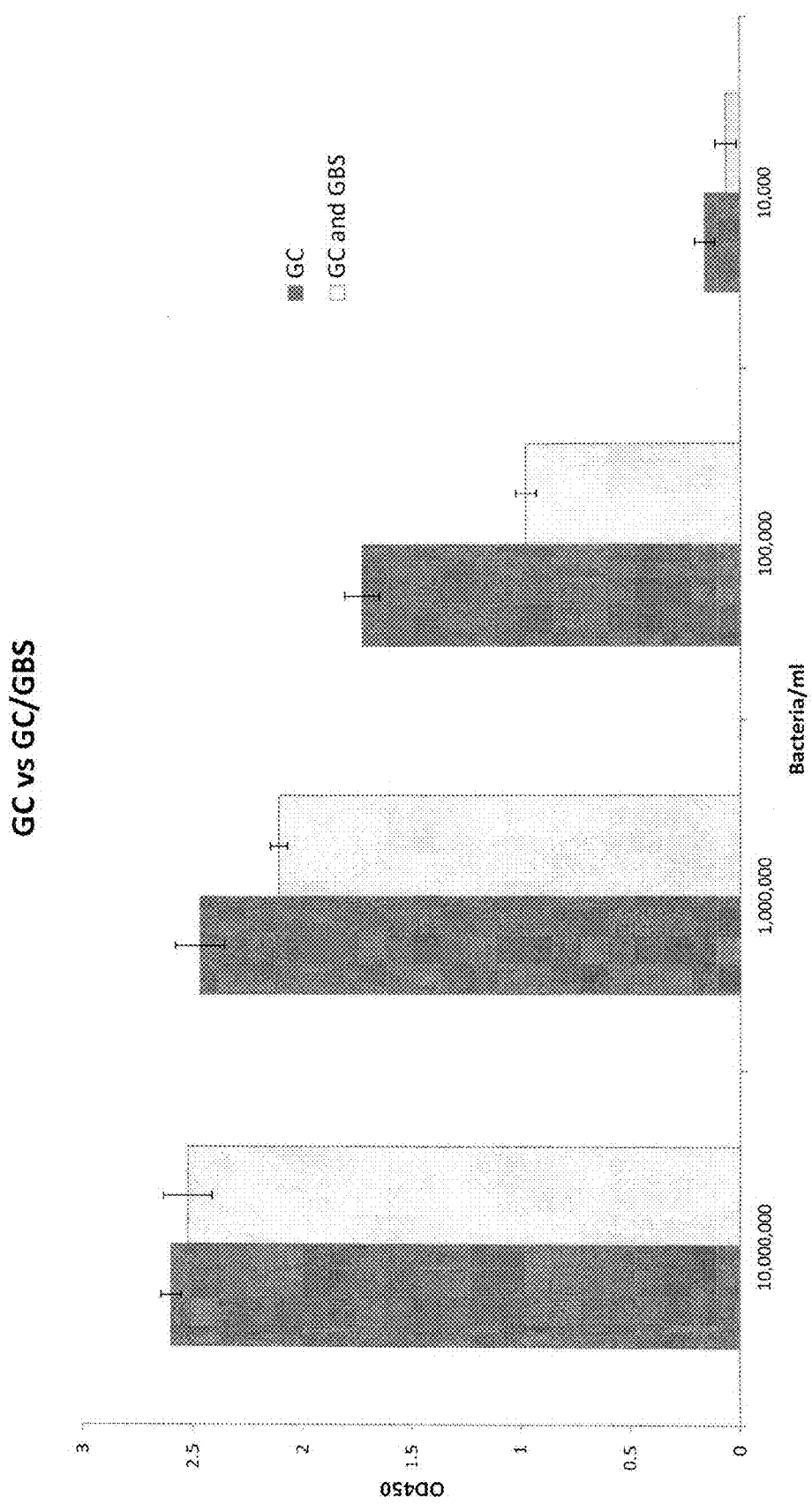
FIG. 15 is a bar showing the detection of *N. gonorrheae* in serial dilutions alone vs. *N. gonorrheae* with GBS as the competing organism, GBS held constant at $10^8$ bacteria/ml to show specificity of the N-Assay, in accordance with the invention.
Figure 16:
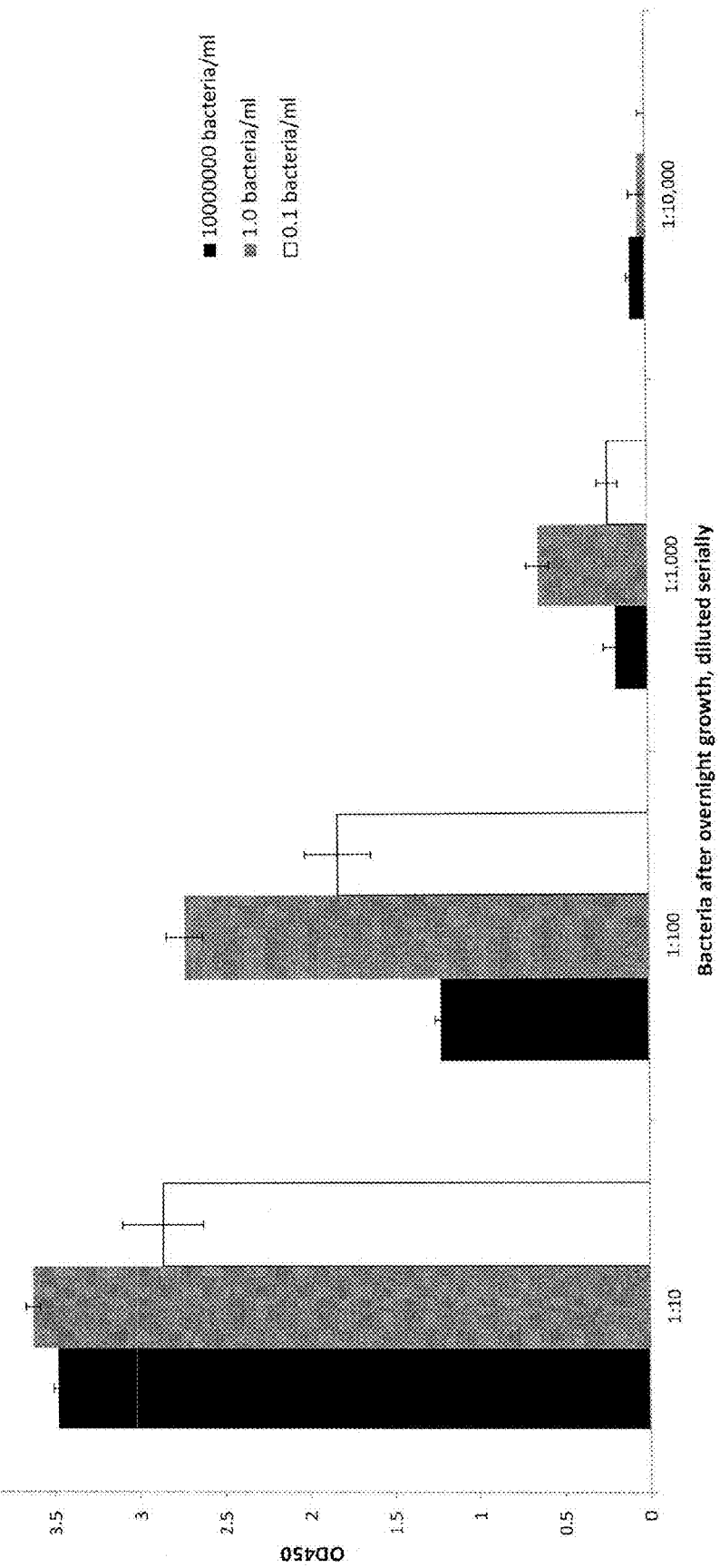
FIG. 16 is a bar showing GBS at three separate concentrations, incubated overnight, then diluted serially, in accordance with the invention.
Figure 17:
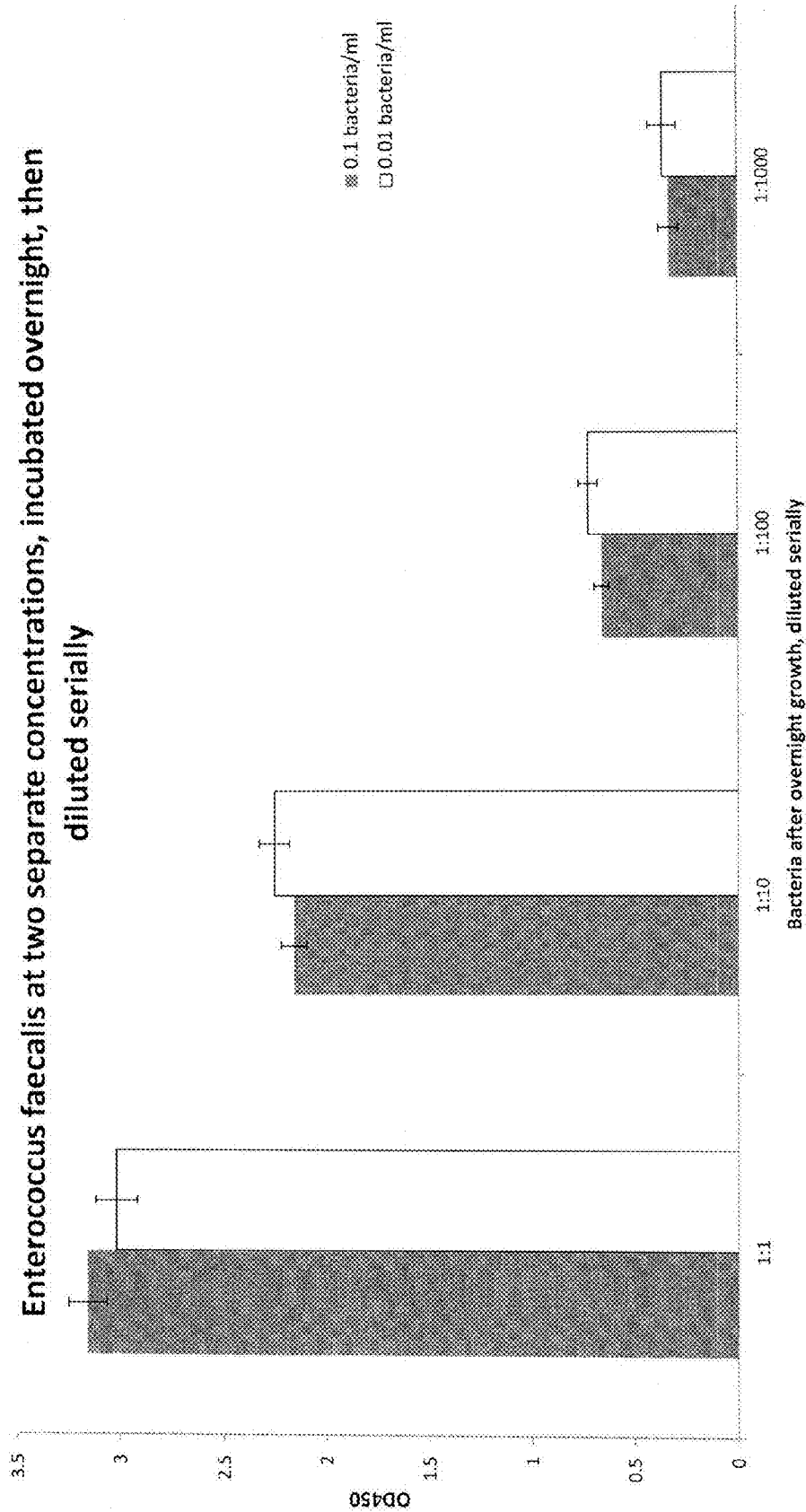
FIG. 17 is a bar showing *E. faecalis* at two separate concentrations, incubated overnight, then diluted serially, in accordance with the invention.
Figure 18:
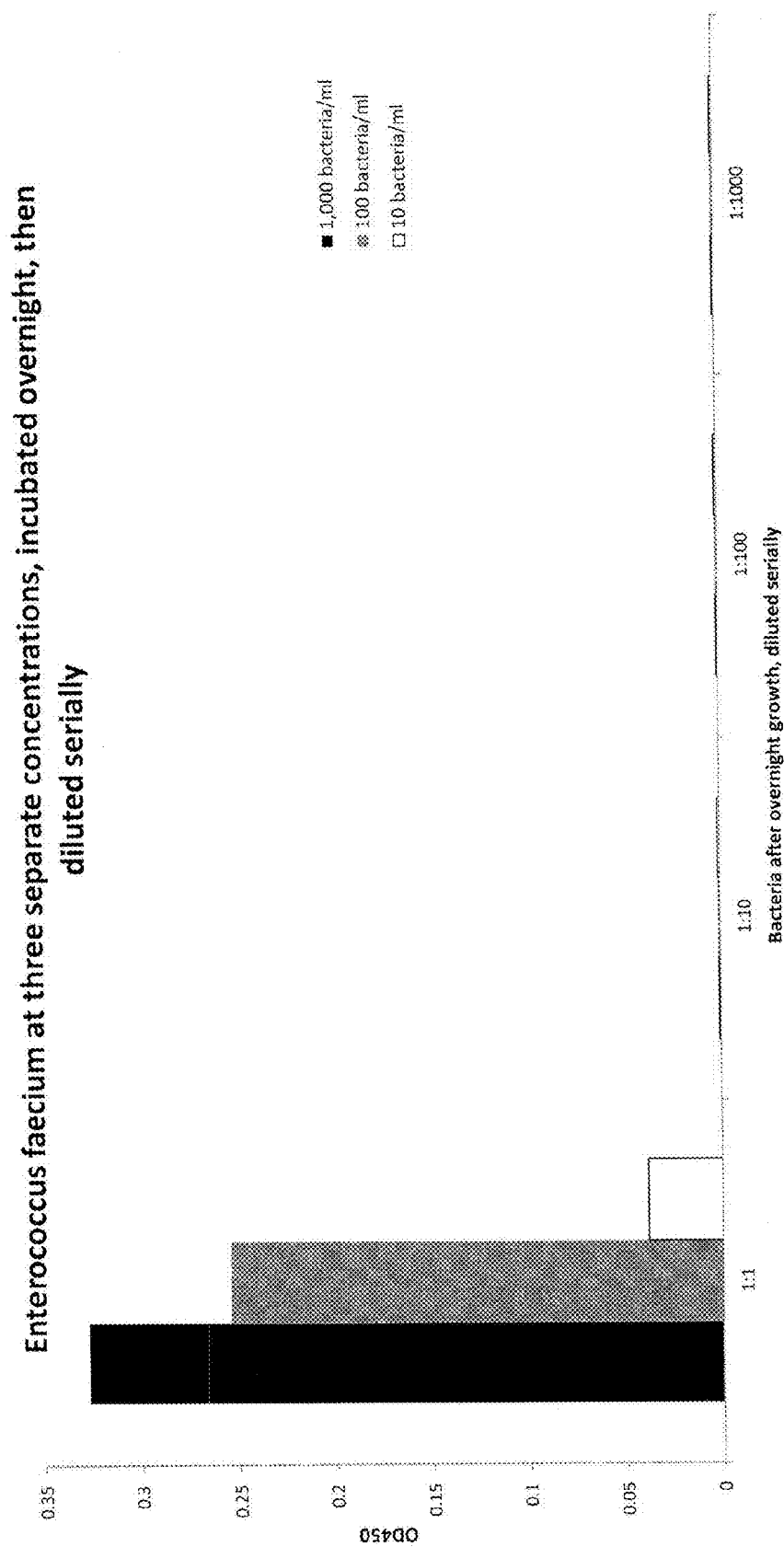
FIG. 18 is a bar showing *E. faedium* at three separate concentrations, incubated overnight, then diluted serially, in accordance with the invention.
Figure 19:
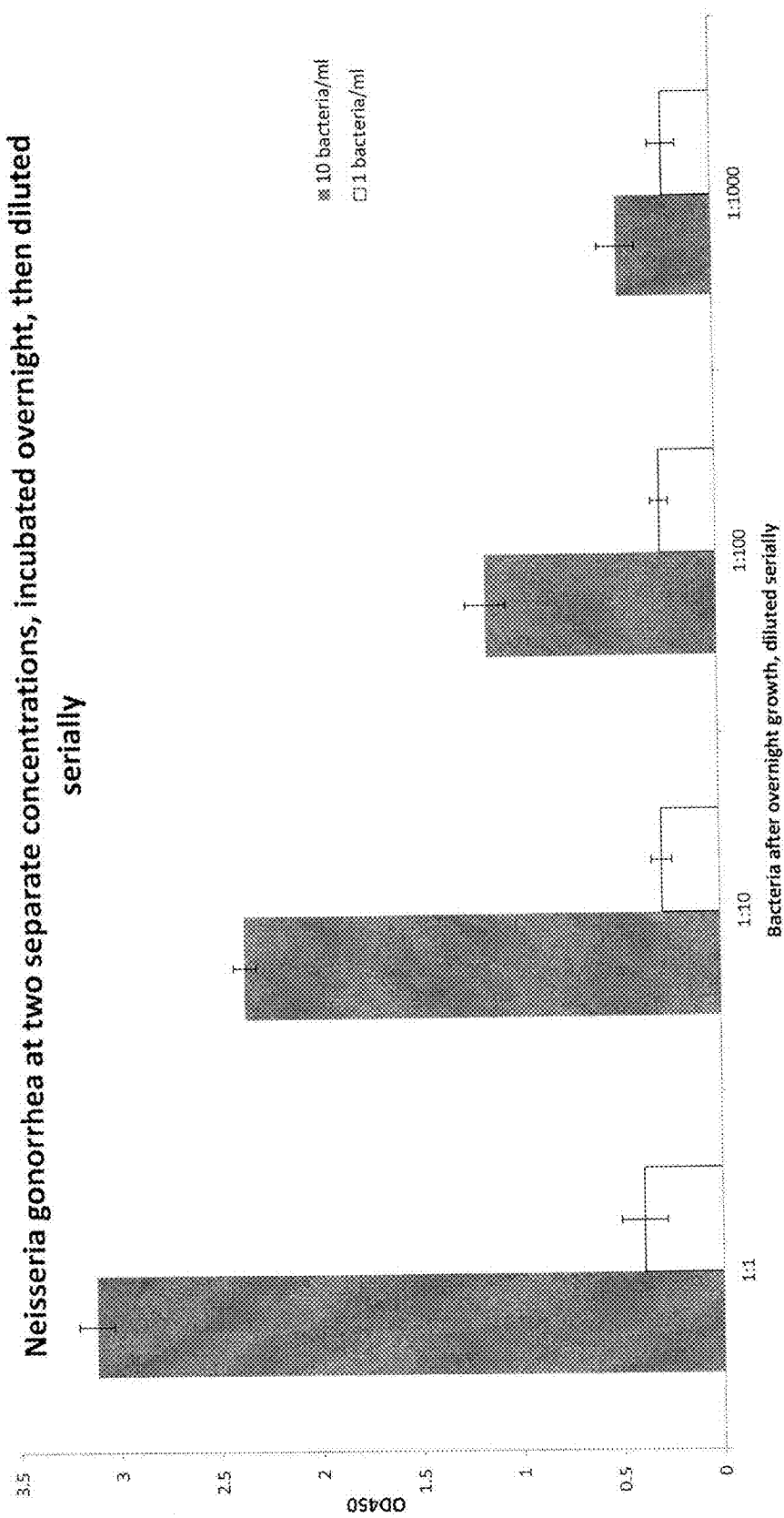
FIG. 19 is a bar showing *N. gonorrheae* at two separate concentrations, incubated overnight, then diluted serially, in accordance with the invention.

To determine the specificity of the assay, suspensions were tested in which the bacterium to be identified was diluted out, but the level of a competing bacterium was held constant at $10^8$ bacteria/ml. Testing of several commonly found vaginal co-colonizers, namely, *Candida albicans*, shown against GBS (FIG. 12), GBS, shown against *E. faecalis* (FIG. 13), *E. coli*, shown against *E. faecium* (VRE) (FIG. 14), and GBS, shown against *N. gonorrhea* (GC) (FIG. 15), revealed little to no interference using the N-Assay.
Increased Sensitivity of N-Assay Following an 18 to 24 Hour Culture Bacteria were diluted serially in nutrient broth (LIM for GBS, Brain Heart Infusion for *E. faecalis, E. faecium* and gonococcal broth for *N. gonorrheae*), and turbidity was determined visually. After 18-24 hours of incubation at 37° C. (in a $CO_2$ incubator for *N. gonorrheae*), the $OD_{630}$ was determined and the results were used to determine the number of bacteria present. Next, 100 μl of each dilution was placed in previously prepared microtiter wells. (Wells had been coated with antibody and then blocked as described above.) The assay proceeded as described above, and plates were read at $OD_{450}$. It was determined that after 18-24 hours of incubation, bacteria were identified at a significantly lower concentration than without an overnight incubation. For GBS, *E. faecalis* and *E. faecium*, dilutions as low as to $10^{-1}$ bacteria/ml were detected. For *N. gonorrheae*, dilutions as low as $10^1$ bacteria/ml were detected (FIGS. 16-19).
Use of N-Assay to Determine Antibiotic Susceptibility Dilutions of individual bacterial isolates with selected antibiotics added were prepared as described above. For the GBS assay, a 0.5 McFarland was prepared in LIM, either in the presence or absence of Clindamycin. Multiple strains of GBS were used, and PCR had been performed previously to identify the presence of resistance genes. In addition, multiple concentrations of the antibiotic were used as the dilutions were prepared in parallel. Samples were then incubated for 24 hours at 37° C., and 100 µl aliquots were used to inoculate microtiter wells for identification, as described above. As shown in Table 1, wells containing GBS sensitive to Clindamycin were found to be negative, while GBS previously found to be resistant to Clindamycin were positive at dilutions down to 100 bacteria/ml.

TABLE 1

Detection of GBS after 18 hour incubation in nutrient broth and 4 µg/ml Clindamycin

| | CFU/ml | | | | |
|---|---|---|---|---|---|
| | 10,000 | 1,000 | 100 | 10 | 1 |
| Clindamycin Resistant Strain (GBS 11276) | | | | | |
| Without Clindamycin Present | + | + | + | + | - |
| With Clindamycin Present | + | + | + | + | - |
| Clindamycin Sensitive Strain (GBS 12386) | | | | | |
| Without Clindamycin Present | + | + | + | + | - |
| With Clindamycin Present | - | - | - | - | - |

These studies were repeated for *E. faecalis, E. faecium* and *N. gonorrheae*. For *E. faecalis* and *E. faecium*, Penicillin G was used to distinguish between *E. faecalis* and *E. faecium*, as *E. faecium* is resistant to Penicillin G. For *N. gonorrheae*, the antibiotic used was ceftriaxone. As shown in Tables 2 and 3, wells containing *E. faecalis* and *N. gonorrheae* were found to be negative, while *E. faecium* were positive at dilutions down to 100 bacteria/ml.

TABLE 2

Detection of *Enterococcus faecalis* and *Enterococcus faecium* after 18 hour incubation in nutrient broth and 8 µg/ml Penicillin G

| CFU/ml | 10,000,000 | 1,000,000 | 100,000 | 10,000 | 1,000 | 100 | 10 | 1 | 0.1 | 0.01 |
|---|---|---|---|---|---|---|---|---|---|---|
| *Enterococcus faecalis* (Penicillin Sensitive) | | | | | | | | | | |
| Without Penicillin Present | + | + | + | + | + | + | + | + | - | - |
| With Penicillin Present | + | + | + | - | - | - | - | - | - | - |
| *Enterococcus faecium* (Penicillin Resistant, i.e., VRE) | | | | | | | | | | |
| Without Penicillin Present | + | + | + | + | + | + | + | + | - | - |
| With Penicillin Present | + | + | + | + | + | + | + | + | - | - |

TABLE 3

Detection of *Neisseria gonorrheae* after 18 hour incubation in nutrient broth and 2 µg/ml Ceftriaxone

| CFU/ml | 10,000 | 1,000 | 100 | 10 | 1 | 0.1 | 0.01 |
|---|---|---|---|---|---|---|---|
| *N. gonorrheae* (Ceftriaxone Sensitive) | | | | | | | |
| Without Ceftriaxone Present | + | + | + | + | - | - | - |
| With Ceftriaxone Present | - | - | - | - | - | - | - |
| *N. gonorrheae* (Ceftriaxone Resistant) | | | | | | | |
| Without Ceftriaxone Present | + | + | + | + | + | + | - |
| With Ceftriaxone Present | + | + | + | + | + | + | - |

It will be appreciated by those skilled in the art that changes could be made to the embodiments described above without departing from the broad inventive concept thereof. It is understood, therefore, that this invention is not limited to the particular embodiments disclosed, but it is intended to cover modifications that are within the spirit and scope of the invention, as defined by the appended claims.

What is claimed is:

1. A method for rapid detection and identification of a target microorganism in a sample, comprising:
    preparing one or more serial dilutions of a sample suspected of containing a microorganism;
    depositing each of the one or more serial dilutions into a separate well of a plurality of wells in a plate, said plurality of wells previously coated with an antibody specific for the target microorganism, incubated overnight at 4° C., washed, adding a blocking agent, and washed a second time;
    gently shaking the plurality of wells for about 15 minutes of time at room temperature;
    washing the plurality of wells;
    adding an enzyme-conjugated antibody specific for the target microorganism to the plurality of wells and incubating the plurality of wells for about 7 minutes;
    washing the plurality of wells;
    adding a substrate specific to the enzyme conjugated to the antibody to the plurality of wells and incubating the plurality of wells for about 3 minutes;
    adding a stop solution to each of the plurality of wells; and
    detecting and identifying the microorganism in wells showing a color change of the substrate, or by reading at $OD_{450}$, wherein the method for detection and identification of the microorganism takes about 30 minutes or less.

2. The method of claim 1, wherein four serial dilutions of the sample containing the microorganism are prepared.

3. The method of claim 1 wherein the enzyme conjugated to the antibody is horseradish peroxidase (HRP) and the substrate specific to the enzyme is tetramethylbenzidine (TMB).

4. The method of claim 1, wherein the target microorganism is selected from the group consisting of bacteria, fungi, yeast, molds and parasites.

5. The method of claim 4, wherein the bacteria is selected from the group consisting of Group B *Streptococcus* (GBS), Groups A, C, F and G *Streptococcus, Staphylococcus aureus, Neisseria gonorrheae, Enterococcus faecalis, Enterococcus faecium*, and *Escherichia coli*; and the fungus is selected from the group consisting of *Candida albicans* and *Pneumocystis pneumonia*.

6. A method for rapid detection and identification of a target microorganism in a sample and determination of susceptibility of the target microorganism to an antibiotic in a sample, comprising:
  preparing one or more serial dilutions of a sample suspected of containing a microorganism in the presence or absence of an antibiotic;
  incubating the one or more serial dilutions of the sample suspected of containing the microorganism in the presence or absence of the antibiotic for about 18 to 24 hours at 37° C.;
  depositing each of the one or more serial dilutions of the sample suspected of containing the microorganism into a separate well of a plurality of wells in a plate, and depositing into separate wells the target microorganism with the antibiotic and the target microorganism without the antibiotic as a positive control, said plurality of wells previously coated with an antibody specific for the target microorganism, incubated overnight at 4° C., washed, adding a blocking agent, and washed a second time;
  gently shaking the plurality of wells for about 15 minutes of time at room temperature;
  washing the plurality of wells;
  adding an enzyme-conjugated antibody specific for the target microorganism to the plurality of wells and incubating the plurality of wells for about 7 minutes;
  washing the plurality of wells;
  adding a substrate specific to the enzyme conjugated to the antibody to the plurality of wells and incubating the plurality of wells for about 3 minutes;
  adding a stop solution to each of the plurality of wells; and
  detecting and identifying in about 30 minutes or less the microorganism in wells showing a color change of the substrate, or by reading at $OD_{450}$ and when an identification has been made, determining the susceptibility of the identified microorganism to the antibiotic by seeing whether those wells containing the identified microorganism and the antibiotic show a color change of the substrate or are read at $OD_{450}$, wherein no color change or a reading at $OD_{450}$ indicates that the identified microorganism is susceptible to the antibiotic, and wherein a color change of the substrate or a reading at $OD_{450}$ indicates that the identified microorganism is not susceptible to the antibiotic.

7. The method of claim 6, wherein four serial dilutions of the sample suspected of containing the microorganism are prepared.

8. The method of claim 6, wherein the enzyme conjugated to the antibody is horseradish peroxidase (HRP) and the substrate specific to the enzyme is tetramethylbenzidine (TMB).

9. The method of claim 6, wherein the target microorganism is selected from the group consisting of bacteria, fungi, yeast, molds and parasites.

10. The method of claim 9, wherein the bacteria is selected from the group consisting of Group B *Streptococcus* (GBS), Groups A, C, F and G *Streptococcus, Staphylococcus aureus, Neisseria gonorrheae, Enterococcus faecalis, Enterococcus faecium*, and *Escherichia coli*; and the fungus is selected from the group consisting of *Candida albicans* and *Pneumocystis*.

11. The method of claim 1, wherein the antimicrobial agent is an antibiotic selected from the group consisting of penicillin, clindamycin, vancomycin, cephalosporin, and ceftriaxone, or other agents exhibiting antimicrobial action.

* * * * *